United States Patent
Lin Wu et al.

(10) Patent No.: US 10,662,413 B2
(45) Date of Patent: May 26, 2020

(54) RECOMBINANT DNA POLYMERASE FOR IMPROVED INCORPORATION OF NUCLEOTIDE ANALOGUES

(71) Applicant: PERSONAL GENOMICS, INC., Grand Cayman (KY)

(72) Inventors: Shiuan-Woei Lin Wu, New Taipei (TW); Ching-Wei Tsai, Taoyuan (TW); Ting-Yueh Tsai, Hsinchu (TW); Jyun-Yuan Huang, Kaohsiung (TW); Chao-Chi Pan, Hsinchu (TW); Li-Chi Chang, Taipei (TW); Ching-Long Hwong, Kaohsiung (TW)

(73) Assignee: PERSONAL GENOMICS, INC., Grand Cayman (KY)

( * ) Notice: Subject to any disclaimer, the term of this patent is extended or adjusted under 35 U.S.C. 154(b) by 0 days.

(21) Appl. No.: 15/798,846

(22) Filed: Oct. 31, 2017

(65) Prior Publication Data
US 2018/0119115 A1 May 3, 2018

Related U.S. Application Data

(60) Provisional application No. 62/415,686, filed on Nov. 1, 2016.

(51) Int. Cl.
C12N 9/12 (2006.01)
C12P 19/34 (2006.01)
C12P 19/30 (2006.01)

(52) U.S. Cl.
CPC ............ *C12N 9/1252* (2013.01); *C12P 19/30* (2013.01); *C12P 19/34* (2013.01)

(58) Field of Classification Search
None
See application file for complete search history.

(56) References Cited

U.S. PATENT DOCUMENTS

| | | |
|---|---|---|
| 5,756,334 A | 5/1998 | Perler et al. |
| 6,287,821 B1 | 9/2001 | Shi et al. |
| 7,361,466 B2 | 4/2008 | Korlach et al. |
| 9,540,688 B2 | 1/2017 | Fu et al. |
| 9,670,243 B2 | 6/2017 | Chiou et al. |
| 2014/0127680 A1 | 5/2014 | Emig et al. |

FOREIGN PATENT DOCUMENTS

EP 0745688 12/1996

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Metzker, Michael L., et al. "Termination of DNA synthesis by novel 3'-modifieddeoxyribonucleoside 5'-triphosphates." Nucleic Acids Research 22.20 (1994): 4259-4267.
Welch, Mike B., et al. "Syntheses of nucleosides designed for combinatorial DNA sequencing." Chemistry-Weinheim-European Journal-5 (1999): 951-960.
Eid, John, et al. "Real-time DNA sequencing from single polymerase molecules." Science 323.5910 (2009): 133-138.
Metzker, Michael L. "Sequencing technologies—the next generation." Nature reviews genetics 11.1 (2010): 31-46.
Guo, Jia, et al. "Four-color DNA sequencing with 3'-O-modified nucleotide reversible terminators and chemically cleavable fluorescent dideoxynucleotides." Proceedings of the National Academy of Sciences 105.27 (2008): 9145-9150.
Bergen, Konrad, et al. "Structures of KOD and 9 N DNA polymerases complexed with primer template duplex." ChemBioChem 14.9 (2013): pp. 1058-1062.
TPO. Taiwan Pat. Appln. No. 106137667. 13 pages.
Chen et al., "Fluorescenc e Polarization in Homogeneous Nucleic Aid Analysis", Genome Research, 1999, pp. 492-498.
Greenough et al., "Adapting capillary gel electrophoresis as a sensitive, high-throughput method to accelerate characterization of nucleic acid metabolic enzymes", 2016, Nucleic Acids Research, 44(2), pp. 1-11.
Werneburg et al., "DNA Polymerase β: Pre-Stready-State Kinetic Analysis and Roles of Arginine-283 in Catalysis and Fidelity", 1996, Biochemistry, pp. 7041-7050.

* cited by examiner

*Primary Examiner* — Richard G Hutson
(74) *Attorney, Agent, or Firm* — Muncy, Geissler, Olds & Lowe, P.C.

(57) ABSTRACT

A composition comprising a recombinant DNA polymerase and 3'-esterified nucleotide analogues is provided. The recombinant DNA polymerase includes an amino acid sequence that is at least 90% homology with 9° N DNA polymerase (SEQ ID NO: 1), and the recombinant DNA polymerase includes at least two mutations at the positions corresponding to amino acid residues 141 and 143 of the 9° N DNA polymerase. A recombinant DNA polymerase is further provided. The recombinant DNA polymerase includes an amino acid sequence that is at least 90% homology with 9° N-III DNA polymerase (SEQ ID NO: 3), and the recombinant DNA polymerase includes one or two mutations at the positions corresponding to amino acid residue 480 and 486 of the 9° N-III DNA polymerase. A method of performing a polymerization reaction is also provided.

5 Claims, 24 Drawing Sheets

Specification includes a Sequence Listing.

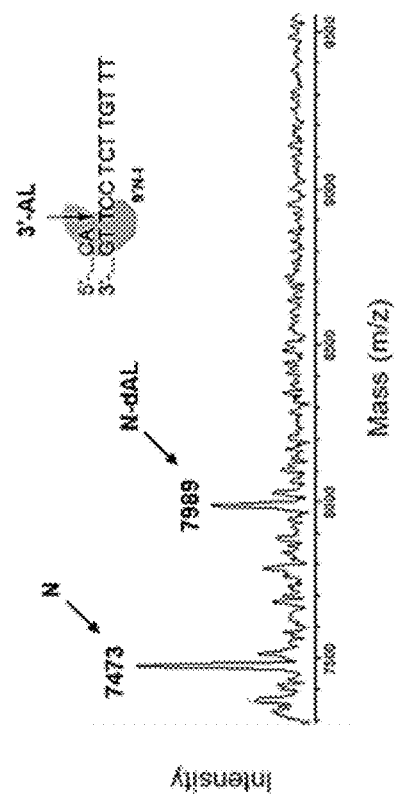
FIG. 1A
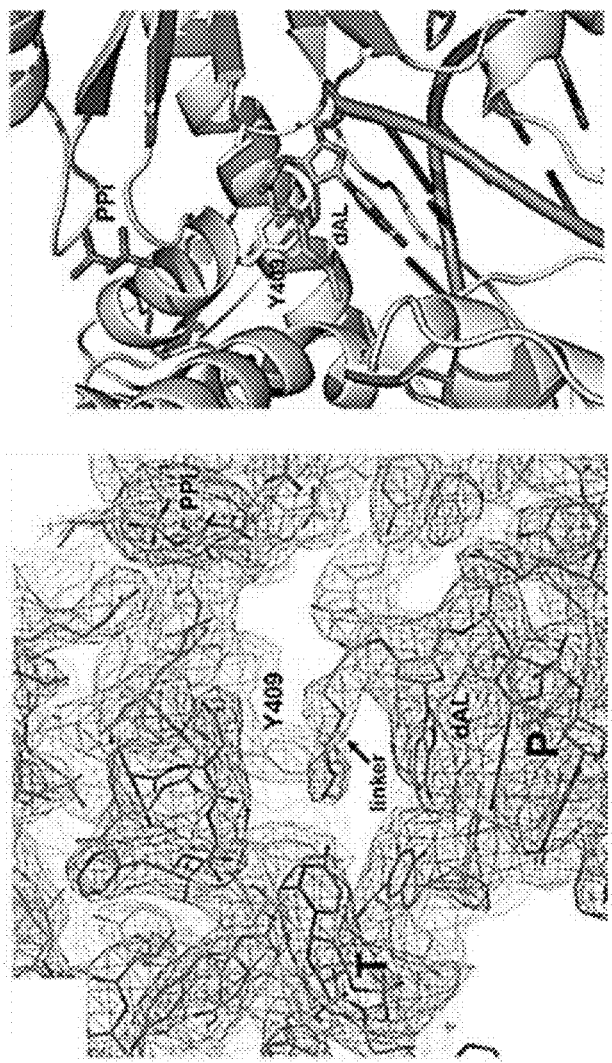
FIG. 1B
FIG. 1C

RECOMBINANT DNA POLYMERASE FOR IMPROVED INCORPORATION OF NUCLEOTIDE ANALOGUES

CROSS-REFERENCE TO RELATED APPLICATIONS

The present application claims priority of U.S. Provisional Patent Application Ser. No. 62/415,686, filed on Nov. 1, 2016, which is incorporated herein by reference in its entirety.

BACKGROUND

DNA polymerase is relied upon by all organisms to replicate and maintain their genomes. They allow high fidelity replication of DNA by detecting complementarity between bases as well as recognizing additional structural features of the base. Three main super families of DNA polymerases exist based upon their amino acid similarity to *E. Coli* DNA polymerases I, II and III. They are called Family A, B and C polymerases, respectively. Family A and B polymerases have a common structural core for the nucleotide binding site.

Early experiments with DNA polymerases revealed difficulties incorporating modified nucleotides such as dideoxy-nucleotides (ddNTPs). Therefore, there are several examples in which DNA polymerases have been modified to increase the rates of incorporation of nucleotide analogues. There is a need to develop a recombinant DNA polymerase capable of incorporating 3'-esterified nucleotide analogues or 3'-ester-dye nucleotide analogues with quencher linked to phosphate group such as 3'-ester-dye/5'-Q, wherein Q represents quencher.

SUMMARY OF THE DISCLOSURE

The present disclosure provides a composition comprising a DNA polymerase derived from the family B DNA polymerase, which possess a 3' editing activity on the nature occurring nucleotides or analogues thereof for DNA strand elongation, and nucleotide analogues with a modification on 3' position of the nucleotide analogues. Optionally, the nucleotide analogue further comprises a modification on 5' position. Specifically, the present disclosure utilizes 9° N and KOD1 DNA polymerases to incorporate 3'-esterified nucleotide analogues. The 9° N and KOD1 DNA polymerases may be able to incorporate 3'-ester-dye nucleotide analogues and can remove the dye after incorporation of the nucleotide analogues. Thus, multiple nucleotide analogues may be incorporated sequentially. Furthermore, the 9° N and KOD1 DNA polymerases may sequentially incorporate 3'-ester-dye nucleotide analogues with quencher linked to phosphate group such as 3'-ester-dye/5'-Q.

In a first aspect, the present disclosure provides a composition comprising a recombinant DNA polymerase and 3'-esterified nucleotide analogues, wherein the recombinant DNA polymerase comprises an amino acid sequence that is at least 90% homology with 9° N DNA polymerase (SEQ ID NO: 1), and the recombinant DNA polymerase comprises at least two mutations at the positions corresponding to the amino acid residues 141 and 143 of the 9° N DNA polymerase.

In a second aspect, the present disclosure provides a recombinant DNA polymerase comprising an amino acid sequence that is at least 90% homology with 9° N-III DNA polymerase (SEQ ID NO: 3), and the recombinant DNA polymerase comprises one or two mutations at the position corresponding to the amino acid residue 480 and 486 of the 9° N-III DNA polymerase.

In a third aspect, the present disclosure provides a method of performing a polymerization reaction comprising the steps of: (a) providing a composition comprising a nucleic acid template, a DNA polymerase of the present disclosure, and optionally a primer; (b) contacting the composition with a 3'-esterified nucleotide analogue, wherein the 3'-esterified nucleotide analogue comprises a linker linked to 3' end through an ester bond; (c) allowing the DNA polymerase to incorporate the 3'-esterified nucleotide analogue in a template-dependent manner into a nascent strand; and (d) allowing the DNA polymerase to remove the linker of the incorporated 3'-esterified nucleotide analogue from the nascent strand.

BRIEF DESCRIPTION OF THE DRAWINGS

FIG. 1A shows a single-base primer extension using 3'-AL nucleotide characterized by MALDI-TOF MS. Reaction with 3'-AL along with the appropriate primer-template yielded single-base extension product of the expected mass (7989 m/z for N-dAL). Peaks for the primer (N) and extension product are indicated.

FIG. 1B shows a binary structure of 9° N-I with primer (P)-template (T) DNA and 3'-AL after incorporation.

FIG. 1C shows a cartoon representation of the active site pocket of 9° N-I binary structure, showing that dAL is linked to the primer with the linker moiety on top of the base.

DETAILED DESCRIPTION OF THE DISCLOSURE

Figure 2:
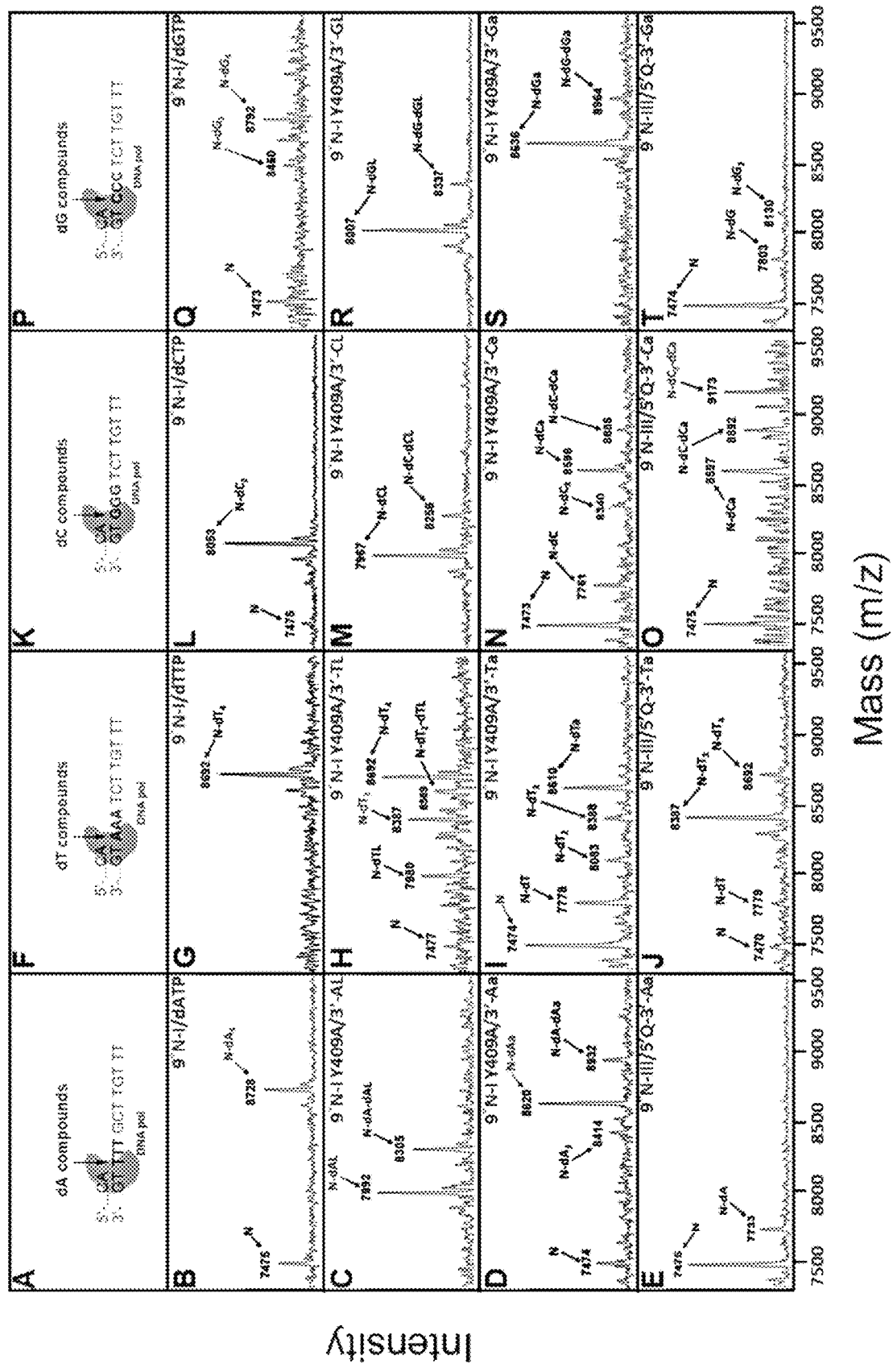
FIG. 2 shows a multiple-base primer extension using native and modified nucleotides characterized by MALDI-TOF MS. Reaction with the nucleotides along with the appropriate primer-template yielded multiple-base extension product of the expected mass, respectively. Peaks for the primer (N) and extension product are indicated. (A, F, K, P) Illustration of multiple-base incorporation into the respective primer-template DNA. (B-E) Extension products of the expected mass of dATP and modified dATP (3'-AL, 3'-Aa and 5'Q-3'-Aa) catalyzed by 9° N-I, 9° N-I Y409A and 9° N-III, respectively. (G-J) Extension products of the expected mass of dTTP and modified dTTP (3'-TL, 3'-Ta and 5'Q-3'-Ta) catalyzed by 9° N-I, 9° N-I Y409A and 9° N-III, respectively. (L-O) Extension products of the expected mass of dCTP and modified dCTP (3'-CL, 3'-Ca and 5'Q-3'-Ca) catalyzed by 9° N-I, 9° N-I Y409A and 9° N-III, respectively. (Q-T) Extension products of the expected mass of dGTP and modified dGTP (3'-GL, 3'-Ga and 5'Q-3'-Ga) catalyzed by 9° N-I, 9° N-I Y409A and 9° N-III, respectively.

In accordance with the present disclosure and as used herein, the following terms are defined with the following meanings, unless explicitly stated otherwise. It is to be understood that both the foregoing general description and the following detailed description are examples and explanatory only and are not restrictive of the subject matter claimed. In this application, the use of the singular includes the plural unless specifically stated otherwise.

In this application, the use of "or" means "and/or" unless stated otherwise. Furthermore, use of the term "including" as well as other forms, such as "includes," and "included" is not limiting.

As used herein, the singular forms "a," "an" and "the" include plural referents unless the context clearly dictates otherwise.

As used herein, the term "incorporation" refers as joining of the modified nucleotide to the free 3' hydroxyl group of a second nucleotide via formation of a phosphodiester linkage with the 5' phosphate group of the modified nucleotide. The second nucleotide to which the modified nucleotide is joined will typically occur at the 3' end of a polynucleotide chain.

As used herein, the terms "modified nucleotides" and "nucleotide analogues", when used in the context of the present disclosure, refer to nucleotides which have been modified at the 3' sugar hydroxyl such that the substituent is larger in size than the naturally occurring 3' hydroxyl group. These terms "modified nucleotides" and "nucleotide analogues" may be used interchangeably.

As used herein, the term "processivity" refers to a characteristic of enzymes that function on polymeric substrates. The degree of processivity refers to the average number of nucleotides added each time the enzyme binds a template. The average DNA polymerase requires about one second locating and binding a primer and template junction. Once it is bound, a non-processive DNA polymerase adds nucleotides at a rate of one nucleotide per second.

As used herein, the term "mutation" as used herein refers to a polypeptide exhibiting change(s) with respect to the native counterpart. For illustrative purposes, a mutant polymerase polypeptide refers to a polymerase polypeptide that originates from a native polymerase after being artificially mutated or altered by man in the laboratory as described herein. Any mutation(s) can be envisaged, including substitution, insertion and/or deletion of one or more nucleotide/amino acid residue(s), non-natural arrangements (e.g. fusion with foreign polypeptides/peptides) as well as any combination of these possibilities. When several mutations are contemplated, they can concern consecutive residues and/or non-consecutive residues.

In some embodiments of the present disclosure, the DNA sequencing system can be performed with the following steps: 1) one fluorescent nucleotide analogue is added onto the nascent primer in the each step of DNA replication by a DNA polymerase, 2) the DNA replication is stalled temperately due to the 3'-end fluorescent attachment, for example, an analogue of a nucleotide or a dinucleotide, 3) the identity of the added nucleotide is recorded by the fluorescent signal presented in its 3'-end attachment, 4) the 3'-end fluorescent moiety is resolved by the exonuclease or esterase activity of the DNA polymerase, and 5) 3'-end hydroxyl group is restored and the last added nucleotide is ready for the next round of nucleotide addition.

When such nucleotide analogue is employed in a modified DNA sequencing system, the fluorescent signal lights up right after the substrate is base-paired with the template at the active site of a DNA polymerase and lasts until the dye moiety is cleaved away from the DNA-polymerase complex by the catalytic editing activity of DNA polymerase. The sequencing procedure of the 3'-dye substrates involves at least two steps of enzymatic reaction, i.e., polymerization and catalytic editing (or ester hydrolysis) activities, to complete each nucleotide addition cycle, and therefore effectively prolong the duration of a fluorescent signal produced by 3'-dye staying in a detection zone. In comparison with the sequencing strategy using 5'-dye labeling substrate (5'-dye), the sequencing method using above mentioned 3'-dye substrate produces longer signal duration, and thus is more accurate.

The recombinant DNA polymerase of the present disclosure may exhibit improvement in the efficiency and/or observed rate of incorporation for one type of modified nucleotide analogues or for a range of different modified nucleotide analogues. For example, the recombinant DNA polymerase of the present disclosure may be capable of incorporating a series of modified nucleotides which have the same 3' substituent but which differ in some other portion of the nucleotide molecule, such as the base portion or the presence of a detectable label. Other polymerases may be capable of incorporating a range of modified nucleotides which carry different 3' substituents.

In a first aspect, there is provided a composition comprising a recombinant DNA polymerase and 3'-esterified nucleotide analogues, wherein the recombinant DNA polymerase comprises an amino acid sequence that is at least 90% homology with 9° N DNA polymerase (SEQ ID NO: 1), and the recombinant DNA polymerase comprises at least two mutations at the positions corresponding to amino acid residues 141 and 143 of the 9° N DNA polymerase.

In some embodiments, the composition of the present disclosure further comprises a primer and dNTP(s).

In some embodiments of the present disclosure, the mutation at the amino acid residue 141 of the 9° N DNA polymerase is D (aspartic acid) 141A (alanine). In some embodiments, the mutation at the amino acid residue 143 of the 9° N DNA polymerase is E (glutamic acid) 143A. In some embodiments, the 9° N DNA polymerase includes an amino acid sequence of SEQ ID NO: 1.

In some embodiments of the present disclosure, the recombinant DNA polymerase is selected from the group consisting of 9° N-I DNA polymerase (SEQ ID NO: 2), 9° N-III DNA polymerase (SEQ ID NO: 3), KOD$^{exo-}$ DNA polymerase (SEQ ID NO: 5), 9° N DNA polymerase (SEQ ID NO: 1) and the mutants thereof, KOD1 DNA polymerase (SEQ ID NO: 4) and the mutants thereof and combinations thereof. In some embodiments of the present disclosure, the present disclosure relates to a thermostable enzyme which is a DNA polymerase obtained from *Thermococcus* sp. 9° N-7 strain. The 9° N-7 is a DNA polymerase with a 3'-5' exonuclease having a molecular weight of about 90-95 kDa as determined by SDS-PAGE. In some embodiments, the polymerase activity is preferably measured by the incorporation of radioactively labeled deoxy nucleotides into an activated DNA; following subsequent separation.

In some embodiments, a 9° N-I DNA polymerase includes an amino acid sequence of SEQ ID NO: 2 and the 9° N-I DNA polymerase (SEQ ID NO: 2) has 99% homology with 9° N DNA polymerase (SEQ ID NO: 1). In some embodiments, the 9° N-I DNA polymerase includes three mutation sites at the amino acid residues 141,143 and 485. In some embodiments, the mutation at the amino acid residue 141 is D141A. In some embodiments, the mutation at the amino acid residue 143 is E143A. In some embodiments, the mutation at the amino acid residue 485 is A485L. In some embodiments, the homology can be identified on the basis of amino acids sequence alignment and/or molecular modeling. Sequence alignments may be compiled using any of the standard alignment tools known in the art, such as for example BLAST etc.

In some embodiments, a 9° N-III DNA polymerase includes an amino acid sequence of SEQ ID NO: 3 and the 9° N-III DNA polymerase (SEQ ID NO: 3) has 99% homology with 9° N DNA polymerase (SEQ ID NO: 1). In some embodiments, the 9° N-III DNA polymerase includes six mutation sites at the amino acid residues 141, 143, 408, 409, 410 and 485. In some embodiments, the mutation at the amino acid residue 141 is D141A. In some embodiments, the mutation at the amino acid residue 143 is E143A. In some embodiments, the mutation at the amino acid residue 408 is L (leucine) 408S (serine). In some embodiments, the mutation at the amino acid residue 409 is Y (tyrosine) 409A. In some embodiments, the mutation at the amino acid residue 410 is P (proline) 410V (valine). In some embodiments, the mutation at the amino acid residue 485 is A485L.

In some embodiments, a KOD$^{exo-}$ DNA polymerase also includes mutations at the amino acid residues 141 and 143. In some embodiments, the KOD$^{exo-}$ DNA polymerase includes an amino acid sequence of SEQ ID NO: 5 and the KOD$^{exo-}$ DNA polymerase (SEQ ID NO: 5) has 90% homology with 9° N DNA polymerase (SEQ ID NO: 1).

In some embodiments of the present disclosure, the recombinant DNA polymerase of the present disclosure, in addition to the mutations at the amino acid residues 141 and 143, further comprises at least one mutation at the amino acid residue 480 or 486 of the 9° N DNA polymerase. In some embodiments, the double mutations at the amino acid residues 480 and 486 confer the recombinant DNA polymerase an enhanced incorporation activity compared to the recombinant DNA polymerase comprises one mutation at the amino acid residues 480 or 486. In some embodiments, the mutation at the amino acid residue 480 is D480A, D480C (cysteine), D480F (phenylalanine), D480G (glycine), D480H (histidine), D480I (isoleucine), D480M (methionine), D480N (asparagine), D480P, D480Q (glutamine), D480R (arginine) or D480S. In some embodiments, the mutation at the amino acid residue 486 is I486A, I486F, I486G, I486H, I486L, I486M, I486P, I486R, I486V, I486W (tryptophan) or I486Y.

In some embodiments of the present disclosure, the recombinant DNA polymerase of the present disclosure in addition to the mutations at the amino acid residues 141 and 143, optionally 480 and/or 486, further comprises at least one mutation at the amino acid residue 282, 325, 408 or 410. In some embodiments, the mutation at the amino acid residue 282 is V282F or V282G. In some embodiments, the mutation at the amino acid residue 325 is E325A, E325M or E325S. In some embodiments, the mutation at the amino acid residue 408 is S408F or S408Y. In some embodiments, the mutation at the amino acid residue 410 is V410A, V410G, V410I or V410P.

In some embodiments of the present disclosure, the recombinant DNA polymerase of the present disclosure in addition to the mutations at the amino acid residues 141 and 143, optionally one or more 480, 486, 282, 325, 408 and 410, further comprises one or more mutation at residue 247, 268, 407, 409, 477, 485, 385, 589, 590, 676 and 742. In some embodiments, the mutation at residue 268 is I268G; the mutation at residue 407 is S407A; the mutation at residue 409 is A409Y; the mutation at residue 477 is K (lysine) 477F or K477Y; the mutation at residue 485 is L485F; the mutation at residue 385 is A385K; the mutation at residue 589 is V589H; the mutation at residue 590 is T (threonine)

590H; the mutation at residue 676 is T676K; and the mutation at residue 742 is E742H or E742R.

The recombinant DNA polymerase of the present disclosure can be produced using any conventional method. In some embodiments of the present disclosure, the recombinant DNA polymerase of the present disclosure may be produced by recombinant DNA techniques. In some embodiments, the production of a recombinant DNA polymerase generally includes the following steps: (1) DNA fragment is isolated and the isolated DNA fragment encodes the active form of the DNA polymerase of the present disclosure; (2) the isolated DNA fragment is then treated with a restriction enzymes to generate fragments with ends capable of being linked to either prokaryotic or eukaryotic host/vector systems; (3) the isolated DNA fragment prepared from the host/vector systems is then mixed with a DNA ligase to create a recombinant DNA; (4) the recombinant DNA is introduced into a host organism; (5) active recombinant DNA polymerases of the present disclosure can be produced by transformed host cultures and recovered either from within host cells or from the culture media if the recombinant DNA polymerase is secreted through the host cell membrane.

In some embodiments of the present disclosure, the recombinant DNA polymerase of the present disclosure may also be produced by recombinant DNA techniques, as the gene encoding this enzyme has been cloned from 9° N-7 genomic DNA. In some embodiments, the coding sequence for 9° N-I DNA polymerase is as SEQ ID NO: 6. In some embodiments, the coding sequence for 9° N-III DNA polymerase is as SEQ ID NO: 7. In some embodiments, the coding sequence for KOD$^{exo-}$ DNA polymerase is as SEQ ID NO: 8.

In some embodiments of the present disclosure, the recombinant DNA polymerase of the present disclosure is capable of incorporating 3'-esterified nucleotide analogues with a linker linked to 3' position through an ester bond. In some embodiments, the nucleotides that will be incorporated more efficiently by the recombinant DNA polymerase of the present disclosure include a purine or pyrimidine base and a ribose or deoxyribose sugar moiety having a removable 3'-OH blocking group covalently attached thereto. In some embodiments, the 3'-esterified nucleotide analogues are 3'-esterified nucleotide, 3'-ester-dye analogue or 3'-ester-dye analogue with quencher linked to phosphate group (3'-ester-dye/5'-Q). In some embodiments, the 3'-ester-dye/5'-Q has the following formula (I):

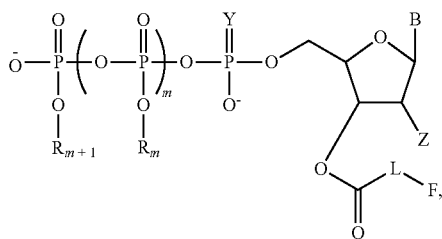

wherein m is an integer and 1≤m≤10, L represents the linker group; Rm and Rm+1 vary as m varies, and when m is larger than 1, Rm refers to a set of functional groups ranging from R1 to Rm, each of Rm may represent independently hydrogen (H) or a functional group consisting of a linker group Lm and a Fm, while Rm+1 may represent hydrogen (H) or a functional group consisting of a linker group Lm+1 and the Fm+1; the F, Fm or Fm+1 is independently a fluorescent dye or a quencher; the linker group Lm or Lm+1 is independently selected from alkyl, alkenyl, alkynyl, aryl, heteroaryl, heterocyclyl, polyethylene glycol, ester, amino, sulfonyl, or a combination thereof;

B represents a base selected from adenine, cytosine, guanine, thymine, uracil, hypoxanthine or 5-methylcytosine;

Z is independently selected from hydrogen, hydroxyl, thiol, halogen, or amino group; and Y in Formula I represents oxygen (O) or sulfur (S).

In some embodiments of the present disclosure, the F, Fm or Fm+1 as the fluorescent dye which is attached to the 3'-end of the nucleotide not only serves as a signal reporter but also functions as a staller in the polymerization. In some embodiments, the quencher linked to phosphate group (3'-ester-dye/5'-Q) is applied to decrease the photo-detectable signals, e.g., fluorescent signals generated from the fluorescent dye, arisen from the label at the 3'-end of the nucleotide, wherein such fluorescent signals are fluorescent background signals in the reagents, and decreasing the background signals can also increase the accuracy. In some embodiments, the linker group harbors a length of 1-50 atoms. In some embodiments of the present disclosure, F in the 3'-esterified nucleotide analogues having the formula (I) represents a photo-detectable label, such as ATTO 488, ATTO 532, ATTO 514, ATTO 520, ATTO 647N, ATTO 633, STAR 488, FAM, Alexa 488, Alexa 532, Alexa 568, Alexa 647, Alexa 660, Alexa 700, FRET dye, Cy3, Cy5, HEX, TAMRA, ROX, JOE, and TET. In some embodiments, the 3'-esterified nucleotide analogue further comprises a first label moiety linked to the linker and optionally a second label moiety linked to 5' phosphate group of the 3'-esterified nucleotide analogue. In some embodiments, compared to the sequencing scheme using 5'-end dye-labeled (5'-dye) substrates, the prolonged signals generated from the above described 3'-end dye-labeled (3'-dye) nucleotide substrates are more accurate.

In an embodiment of the first aspect, the composition of the present disclosure includes the recombinant DNA polymerase with an amino acid sequence that is at least 90% homology with 9° N DNA polymerase (SEQ ID NO: 1), for example, the 9° N-I DNA polymerase (SEQ ID NO: 2), the 9° N-III DNA polymerase (SEQ ID NO: 3), the KOD1 DNA polymerase (SEQ ID NO: 4) or the KOD$^{exo-}$ DNA polymerase (SEQ ID NO: 5), and the 3'-esterified nucleotide analogues such as 3'-ester-dye analogue or 3'-ester-dye analogue with quencher linked to phosphate group (3'-ester-dye/5'-Q).

In a second aspect, the present disclosure provides a recombinant DNA polymerase comprising an amino acid sequence that is at least 90% homology with 9° N-III DNA polymerase (SEQ ID NO: 3), and the recombinant DNA polymerase comprises one or two mutations at the position corresponding to the amino acid residue 480 and 486 of the 9° N-III DNA polymerase. In some embodiments, the 9° N-III DNA polymerase includes mutations at the amino acid residues 141 and 143. In one embodiment, the 9° N-III DNA polymerase includes an amino acid sequence of SEQ ID NO: 3.

In some embodiments, the recombinant DNA polymerase comprises double mutations at the amino acid residues 480 and 486 and the recombinant DNA polymerase with double mutations at the amino acid residues 480 and 486 has the enhanced incorporation activity compared with the recombinant DNA polymerase with single mutation at the amino acid residues 480 or 486. In some embodiments, the mutation at the amino acid residue 480 is D480A, D480C, D480F, D480G, D480H, D480I, D480M, D480N, D480P, D480Q, D480R or D480S. In some embodiments, the mutation at the amino acid residue 486 is I486A, I486F, I486G, I486H, I486L, I486M, I486P, I486R, I486V, I486W or I486Y. In some embodiments of the present disclosure, the recombinant DNA polymerase of the present disclosure in addition to the mutation at the amino acid residue 480 and/or 486, further comprises at least one mutation at the amino acid residue 282, 325, 408 or 410. In some embodiments, the mutation at the amino acid residue 282 is V282F or V282G. In some embodiments, the mutation at the amino acid residue 325 is E325A, E325M or E325S. In some embodiments, the mutation at the amino acid residue 408 is S408F or S408Y. In some embodiments, the mutation at the amino acid residue 410 is V410A, V410G, V410I or V410P.

In some embodiments of the present disclosure, the recombinant DNA polymerase of the present disclosure in addition to the mutations at the amino acid residues 480 and 486, optionally one or more 282, 325, 408 or 410, comprises one or more mutation at residue 247, 268, 407, 409, 477, 485, 385, 589, 590, 676 and 742. In some embodiments, the mutation at residue 268 is I268G; the mutation at residue 407 is S407A; the mutation at residue 409 is A409Y; the mutation at residue 477 is K477F or K477Y; the mutation at residue 485 is L485F; the mutation at residue 385 is A385K; the mutation at residue 589 is V589H; the mutation at residue 590 is T590H; the mutation at residue 676 is T676K; and the mutation at residue 742 is E742H or E742R.

The recombinant DNA polymerase of the present disclosure can improve in the desired activity of the DNA polymerase and especially improve in the rate of incorporation of nucleotide analogues having large substituents at the 3' position.

Mutation(s) can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by chemical synthetic techniques (e.g. resulting in a synthetic nucleic acid molecule). According to some embodiments, the mutation(s) contemplated by the present disclosure encompass deletion(s) and/or substitution(s) of one or more amino acid residue(s) involved directly or indirectly in at least one enzymatic activity exhibited by a native DNA polymerase. In one embodiment, the mutation increases enzymatic activity such as the polymerase activity. In the context of the disclosure, the resulting mutant polymerase polypeptide globally retains a high degree of identity (e.g. at least 90%) with the corresponding native DNA polymerase in the non-mutated portions.

In some embodiments of the present disclosure, the recombinant DNA polymerase of the present disclosure is capable of incorporating 3'-esterified nucleotide analogues with a linker linked to 3' position through an ester bond. In some embodiments, the 3'-esterified nucleotide analogues are 3'-esterified nucleotide or 3'-ester-dye analogue with quencher linked to phosphate group (3'-ester-dye/5'-Q). The embodiments of the 3'-ester-dye/5'-Q having formula (I) and the quencher are those as described herein.

In a third aspect, there is provided a method of performing a polymerization reaction comprising the steps of: (a) providing a composition comprising a nucleic acid template, a DNA polymerase of the present disclosure, and optionally a primer; (b) contacting the composition with a 3'-esterified nucleotide analogue, wherein the 3'-esterified nucleotide analogue comprises a linker linked to 3' end through an ester bond; (c) allowing the DNA polymerase to incorporate the 3'-esterified nucleotide analogue in a template-dependent manner into a nascent strand; and (d) allowing the DNA polymerase to remove the linker of the incorporated 3'-esterified nucleotide analogue from the nascent strand.

The embodiments of the DNA polymerase, the 3'-ester-dye/5'-Q having formula (I) and the quencher are those as described herein.

In some embodiments, the polymerization reaction is used for polymerase chain reaction, qPCR, dPCR, q-RT-PCR, nucleic acid synthesis, sequencing by synthesis, pyrosequencing, proton release sequencing, single molecule real-time sequencing (SMRT), fluorescence imaging on nucleic acids, single-nucleotide polymorphism (SNP) genotyping or real-time fluorescence quenching on nucleic acids.

In some embodiments of the present disclosure, the composition of the present disclosure comprising a recombinant DNA polymerase and 3'-esterified nucleotide analogues or the recombinant DNA of the present disclosure may be used to incorporate modified nucleotide analogues into a polynucleotide chain. The modified nucleotide analogues of the present disclosure have been modified at the 3' sugar hydroxyl such that the substituent is larger in size than the naturally occurring 3' hydroxyl group. The modified nucleotide analogues of the present disclosure may be used to detect the sequence of a DNA template. In some embodiments, the recombinant DNA polymerase of the present disclosure may be used in sequencing applications and may be used in conjunction with any type of array-based sequencing technology which requires the utility of a DNA polymerase to incorporate nucleotides into a polynucleotide chain. In some embodiments, the composition of the present disclosure comprising a recombinant DNA polymerase and 3'-esterified nucleotide analogues or the recombinant DNA of the present disclosure may be used for nucleic acid sequencing on any type of array formed by immobilizing nucleic acid on a solid support.

The foregoing outlines features of several embodiments so that those skilled in the art may better understand the aspects of the present disclosure. Those skilled in the art should appreciate that they may readily use the present disclosure as a basis for designing or modifying other composition for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

EXAMPLE

Abbreviation

TABLE 1

The following table lists the abbreviations used herein.

| Abbreviation | Meaning |
| --- | --- |
| 9°N-I | 9°N DNA polymerase with mutation sites at D141A, E143A and A485L |
| 9°N-III | 9°N DNA polymerase with mutation sites at D141A, E143A, L408S, Y409A, P410V and A485L |
| Bst-Lg | Bst Large fragment DNA polymerase |
| Bsu | Bsu DNA polymerase |
| Klenow | Klenow (exo-) fragment DNA polymerase |
| Taq | Taq DNA polymerase |
| Tfl | Tfl DNA polymerase |

TABLE 1-continued

The following table lists the abbreviations used herein.

| Abbreviation | Meaning |
|---|---|
| THN | Therminator |
| Tth | Tth DNA polymerase |
| Vent | Vent (exo-) DNA polymerase |
| 3'-NL | dNTP with 3'-ester-linker |
| 3'-Na | dNTP with 3'-ester-ATTO532 |
| 3'-AL | dATP with 3'-ester-linker |
| 3'-TL | dTTP with 3'-ester-linker |
| 3'-CL | dCTP with 3'-ester-linker |
| 3'-GL | dGTP with 3'-ester-linker |
| 3'-Aa-d | dATP with 3'-ester-ATTO532, ATTO520, ATTO514 and STAR488, respectively |
| 3'-Ta-d | dTTP with 3'-ester-ATTO532, ATTO520, ATTO514 and STAR488, respectively |
| 3'-Ca-d | dCTP with 3'-ester-ATTO532, ATTO520, ATTO514 and STAR488, respectively |
| 3'-Ga-d | dGTP with 3'-ester-ATTO532, ATTO520, ATTO514 and STAR488, respectively |
| 5'Q-3'-Na | dNTP with 5'-quencher/3'-ester-ATTO532 |
| 5'Q-3'-Nd | dNTP with 5'-quencher/3'-ester-STAR488 |
| 5'Q-3'-Aa | dATP with 5'-quencher/3'-ester-ATTO532 |
| 5'Q-3'-Ta | dTTP with 5'-quencher/3'-ester-ATTO532 |
| 5'Q-3'-Ca | dCTP with 5'-quencher/3'-ester-ATTO532 |
| 5'Q-3'-Ga | dGTP with 5'-quencher/3'-ester-ATTO532 |

Chemicals and Enzymes

All chemicals were purchased from Sigma-Aldrich unless otherwise indicated. Oligonucleotides used as primers or templates were commercially synthesized. Nucleotide analogues used in the present disclosure were all synthesized from Personal Genomics Inc. Therminator, Vent (exo−), Bst-Lg, Bsu, Taq, and Klenow (exo−) fragment DNA polymerases were obtained from New England Biolabs. Tfl and Tth DNA polymerases were obtained from Promega.

Protein Expression and Purification

Plasmids DNA encoding 9° N-I, 9° N-III and KOD$^{exo-}$ were transformed into *E. coli* strain BL21 and grown in 5 ml of instant TB medium to induce expression. Cells were harvested for 14 hours and disrupted using glass beads. Cleared lysate were obtained after centrifugation. 9° N-III mutants and KOD$^{exo-}$ mutants contained a 6× histidine tag on the C-terminus were purified using nickel-nitrilotriacetic acid (Ni-NTA) resins. The bound protein was eluted using elution buffer. Purified 9° N-III and KOD$^{exo-}$ mutants were stored in aliquots at −80° C.

Site-Directed and Saturation Mutagenesis

Site-directed saturation mutagenesis experiments were carried out using Phusion high-fidelity DNA polymerase (Thermo Fisher Scientific) with the recombinant expression vector pET28b (−) containing the 9° N-III gene as a template. For saturation mutagenesis, a pair of well-designed complementary primers at a ratio of 1:1 was used. All primers were synthesized by Mission Biotech (Taiwan). The mutagenesis reactions were performed in 20-μL reactions under the same conditions. The reactions contain 1× HF buffer, 200 μM each dNTP, 100 ng template, 2 μM each mixed primer, and 0.06 U/μL Phusion polymerase. The temperature program used was 98° C. for 2 min followed by 35 cycles of 30 s at 98° C., 30 s at 55° C., and 5 min at 72° C., and finished with a final incubation at 72° C. for 10 min. After amplification, the reaction mixture was digested with DpnI (Thermo Fisher Scientific) at 37° C. for 1 hour to digest methylated parental DNA. 5 μL of DpnI-digested mixtures were used to transform *E. coli* DH5a chemical competent cells. Cells were thawed on ice, 5 μl, of reaction added, mixed gently, then incubated on ice for 30 min. Cells were heat shocked at 42° C. for 60 secs, then placed on ice again for 2 min. Next, 500 μL of SOC media was added, and transformed cells incubated at 37° C. with shaking for 30 mins. Transformed cells were pelleted by centrifugation, and resuspend in 150 μL of SOC medium. Finally, transformed cells were plated onto LB agar plates containing Kanamycin (50 μg/mL) and incubated overnight at 37° C. Generally, 50-100 colonies appeared on the plate the next day. The transformed culture was plated on LB agar plates supplemented with 50 μg/mL Kanamycin. Sequence analysis was performed by Mission Biotech (Taiwan).

MALDI-TOF MS Analysis

Mass measurement of DNA after nucleotide incorporation was made on Bruker AutoFlex III smartbeam TOF/TOF200 system. Primer at 10 μM was preannealed with the template at a 1:1 ratio in 10× reaction buffer (100 mM Tris-HCl, 100 mM KCl, 20 mM MnCl$_2$, and pH 7.5) before mixing with nucleotides and DNA polymerase. The reaction was heated to 95° C. for 1 min, 55° C. for 2 mins and then cooled to 30° C. for 2 mins. 0.4 μM of DNA polymerase was added into the primer/template complex and incubated on ice for 30 mins. 40 μM of specific modified compound was added into polymerase reactions on ice and incubated at 60° C. for 60 mins. The reaction was quenched with 2 μL of acetonitrile for stop reaction. Before MS analysis, the reaction product was cleaned up with Micro Bio-Spin™ 30 column (RNase-Free, Bio-Rad, 7326251).

Crystallization and Structure Determination

One day before crystallization, the annealed DNA as described above were added to a mixture of 9° N-I and buffer with CaCl$_2$, and then incubated on ice for 10 mins. Finally, 3'-AL was added into the mixture and incubated at 4° C. overnight. The mixtures were mixed at a ratio of [Pol]:[DNA]:[dNTP]:[Ca$^{2+}$]=1:1:10:20. The crystals appeared in weeks with hanging drop vapor diffusion at room temperature. The crystal was collected from the condition of mixing 2 μL of protein-DNA complex (10 mg/ml in 50 mM HEPES at pH 7.5, 150 mM KCl, and 2 mM DTT) with 1.5 μL reservoir (30-37.5% MPD, 0-10% glycerol, 100 mM NaCl and 0-10 mM CaCl$_2$). X-ray diffraction experiment was performed at NSRRC (Taiwan) and the collected data were processed with HKL2000 and then molecular replaced with CCP4. The protein model built was then refined by using program Coot and calculated with CCP4.

Fluorescence Polarization Assay

The fluorescence polarization (FP) experiment was performed and calculated based on the established method (Chen et al., Genome Research, 9:492-498 (1999)). Primer at 10 μM was preannealed with the template at a 1:1 ratio in 10× reaction buffer (200 mM Tris-HCl, 100 mM (NH$_4$)$_2$SO$_4$, 100 mM KCl, 20 mM MnCl$_2$, pH 7.5) before mixing with nucleotides and DNA polymerase. The reaction was heated to 95° C. for 1 min, 55° C. for 2 mins and then cooled to 30° C. for 2 mins. 1 μM of DNA polymerase was added into the primer/template complex and incubated on ice for 30 mins. 0.5 μM of specific modified compound was added into polymerase reactions on ice and incubated at 60° C. for 60 mins. Before fluorescence measurement, the reaction was quenched with 1.4 μL of 0.5M EDTA for stop reaction.

Primer Extension

All DNA substrates used in the extension assays are listed in Table 2 and were synthesized from Integrated DNA Technologies. The primers used for incorporation and processivity assays were synthesized with a 5'-6-carboxyfluorescein (FAM) label for fluorescence detection. Experimental procedures were described briefly as follows: FAM-labeled primer at 30 nM was preannealed with the template at a 1:6 ratio in 1× ThermoPol buffer (20 mM Tris-HCl, 10 mM $(NH_4)_2SO_4$, 10 mM KCl, 2 mM $MgSO_4$, 0.1% Triton X-100 pH 7.5) before mixing with dNTPs and DNA polymerase. The reaction was heated to 85° C. for 5 mins, then cooled to 25° C. at 0.1° C./s. DNA polymerase with indicated amount was added into the primer/template complex and incubated on ice for 30 mins. Specific modified compound was added into polymerase reactions on ice and incubated at their appropriate temperature for 10 mins. The reaction was quenched with 1.25 µL of stop solution (0.5 mM EDTA). The fluorescence and size of extended products were determined by capillary electrophoresis on an ABI 3500 genetic analyzer (Applied Biosystem) using POP-7 polymer and 36-cm length capillary. Capillary gel electrophoresis and sample are prepared as previous described (Nucleic Acids Res. 2016. 44(2):e15). Data were analyzed using GeneMapper v4.0 with specific detection parameters and displayed as a linear-log plot of product formation versus compound concentration. Polymerase end point (PEP) assays were performed in triplicate, for each DNA polymerase/modified nucleotide to calculate the average IC50±SD.

TABLE 2

Oligonucleotide substrates

| Primer | Label | Sequence |
|---|---|---|
| Primer_FAM_50 nt | 5'-FAM | AGTGAATTCGAGCTCGGTACCCGGGGATCCT CTAGAGTCGACCTGCAGGC (SEQ ID NO: 9) |
| M13-Fam-50 | 5'-FAM | CGAGCACGTATAACGTGCTTTCCTCGTTGGA ATCAGAGCGGGAGCTAAAC (SEQ ID NO: 10) |

| Template | | Sequence |
|---|---|---|
| Temp_(A) 67 nt | none | TTGCTCGTTTGCTGGGAGCCTGCAGGTCGA CTCTAGAGGATCCCCGGGTACCGAGCTCGA ATTCACT (SEQ ID NO: 11) |
| Temp(G)_ 67 nt | none | TTGCTCGTTTGCTAAAGGCCTGCAGGTCGAC TCTAGAGGATCCCCGGGTACCGAGCTCGAAT TCACT (SEQ ID NO: 12) |
| Temp(T)_67 nt | none | TTGCTCGTTTGCTGGGTGCCTGCAGGTCGAC TCTAGAGGATCCCCGGGTACCGAGCTCGAAT TCACT (SEQ ID NO: 13) |
| Temp(C)_67 nt | none | TTGCTCGTTTGCTGGGCGCCTGCAGGTCGA CTCTAGAGGATCCCCGGGTACCGAGCTCGA ATTCACT (SEQ ID NO: 14) |
| M13-100 nt | none | ATGGACAGACTCTTTTACTCGGTGGCCTCAC TGATTATAAAAACACTTCTCAAGATTCTGGC GTACCGTTCCTGTCTAAAATCCCTTTAATCG GCCTCCTGTTTAGTCCCGCTCTGATTCCAAC GAGGAAAGCACGTTATACGTGCTCG (SEQ ID NO: 15) |

Pre-Steady State Kinetic Assay

The rate of incorporation of the correct base onto the 25/36 mer duplex was determined in a reaction. The reaction was initiated by combining the solution containing the enzyme and DNA substrate with the second solution containing $Mg^{2+}$/dNTP. The reaction was quenched with 0.25 M EDTA (final concentration), pH 8.0. A rapid quench instrument (KinTek Instrument Corp., State College, Pa.) was used for reaction times ranging from 20 ms to 20 s.

DNA Elongation with Gel Electrophoresis

A sample of the quenched reaction mixture was mixed with an equal volume of the gel loading buffer, denatured at 85° C. for 5 min, and loaded onto a 16% acrylamide-7 M urea gel. The substrate and product bands were quantitated with α-scanner (Betagen) as described by Werneburg et al. (1996).

DNA Processivity Assay

Linear single-stranded DNA fragment prepared from M13mp18 DNA was used as the template in processivity assays. The forward primer-A and reverse primer-B were used to amplify the specific region of M13mp18 DNA (150 bp). In order to obtain single-stranded DNA, the PCR fragment was treated with lambda exonuclease at 37° C. for 1 hr. Because of forward primer-A was phosphorylated, the new synthesis strand with primer-A will be digested.

Single Base Incorporation of 3'-Esterified Nucleotide

In the present disclosure, the single base incorporation of 3'-AL, a 3'-ester-ethylene glycol linker modified dATP, was characterized by MALDI-TOF mass spectrometry and X-ray crystallography. As shown in FIG. 1A, the increase of molecular mass of primer DNA was obtained after reaction of 9° N-I DNA polymerase with 3'-AL in the presence of a template DNA at 60° C. for 60 min, in which the primer peak N (7473 m/z) was shifted to an extension product N-dAL (7989 m/z). Furthermore, the incorporation of single base was characterized with three-dimensional structure as indicated in FIG. 1B, in which 3'-AL incorporated into primer DNA with its linker moiety still connected at 3'-OH of dATP without being cleaved.

Multiple Bases Incorporation of 3'-Esterified Nucleotide

In the present disclosure, the multiple bases incorporation of 3'-esterified dNTP (3'-NL, 3'-Na and 5'Q-3'-Na) and natural dNTP was characterized by MALDI-TOF mass spectrometry as shown in FIG. 2. The increase of molecular mass of primer DNA was obtained after reaction of 9° N DNA polymerase with the native and modified nucleotides at 60° C. for 60 min. For dNTP, the extension products of dATP (N-$dA_4$, 8728 m/z), dTTP (N-$dT_4$, 8692 m/z), dCTP (N-$dC_2$, 8053 m/z), and dGTP (N-$dG_3$, 8460 m/z and N-$dG_4$, 8792 m/z) were obtained from 9° N-I catalysis. For 3'-NL, the extension products of 3'-AL (N-dAL, 7992 m/z and N-dA-dAL, 8305 m/z), 3'-TL (N-dTL, 7980 m/z, N-$dT_3$, 8387 m/z, N-$dT_2$-dTL, 8589 m/z, and N-$dT_4$, 8692 m/z), 3'-CL (N-dCL, 7967 m/z, N-dC-dCL, 8256 m/z), and 3'-GL (N-dGL, 8007 m/z and N-dG-dGL, 8337 m/z) were obtained from 9° N-I Y409A catalysis. For 3'-Na, the extension products of 3'-Aa (N-$dA_3$, 8414 m/z, N-dAa, 8620 m/z, and N-dA-dAa, 8932 m/z), 3'-Ta (N-dT, 7778 m/z, N-$dT_2$, 8083 m/z, N-$dT_3$, 8388 m/z, and N-dTa, 8610 m/z), 3'-Ca (N-dC, 7761 m/z, N-$dC_3$, 8340 m/z, N-dCa, 8596 m/z, and N-dC-dCa, 8885 m/z), and 3'-Ga (N-dGa, 8636 m/z and N-dG-dGa, 8964 m/z) were obtained from 9° N-I Y409A catalysis. For 5'Q-3'-Na, the extension products of 5'Q-3'-Aa (N-dA, 7733 m/z), 5'Q-3'-Ta (N-dT, 7779 m/z, N-$dT_3$, 8387 m/z, and N-$dT_4$, 8692 m/z), 5'Q-3'-Ca (N-dCa, 8597 m/z, N-dC-dCa, 8892 m/z, and N-$dC_2$-dCa, 9173 m/z), and 5'Q-3'-Ga (N-dG, 7803 m/z and N-$dG_2$, 8130 m/z) were obtained from 9° N-III catalysis.

Figure 3A:
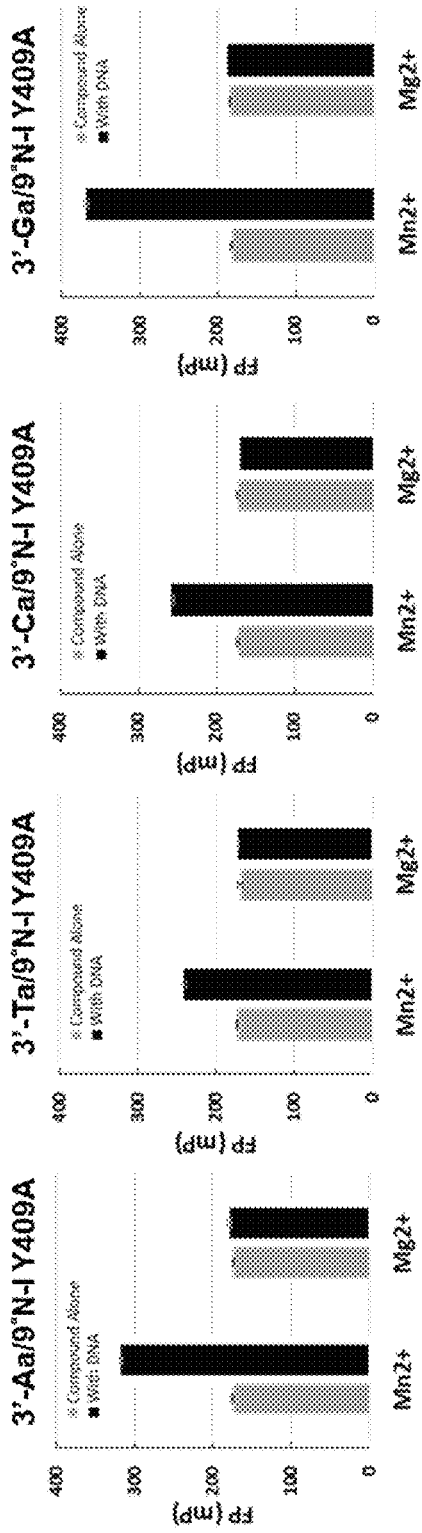
FIG. 3A shows a fluorescence polarization (FP) activity of the modified nucleotides after incorporation. FP activity of 3'-Na catalyzed by 9° N-I Y409A in the presence of $Mn^{2+}$ and $Mg^{2+}$, respectively.
Figure 3B:
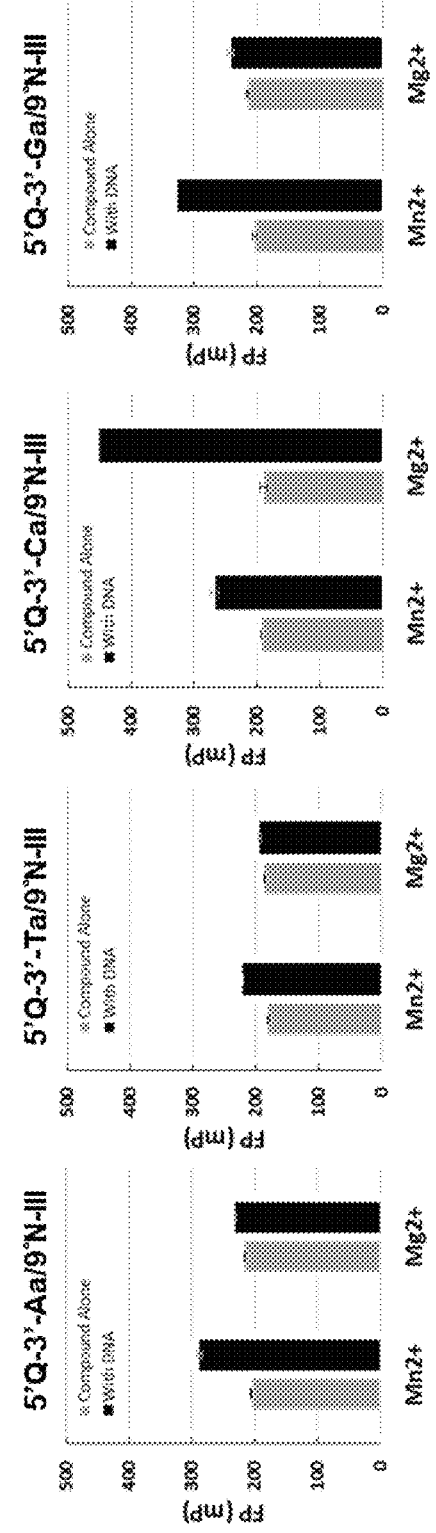
FIG. 3B shows a fluorescence polarization (FP) activity of the modified nucleotides after incorporation. FP activity of 5'Q-3'-Na catalyzed by 9° N-III in the presence of $Mn^{2+}$ and $Mg^{2+}$, respectively.
Figure 3D:
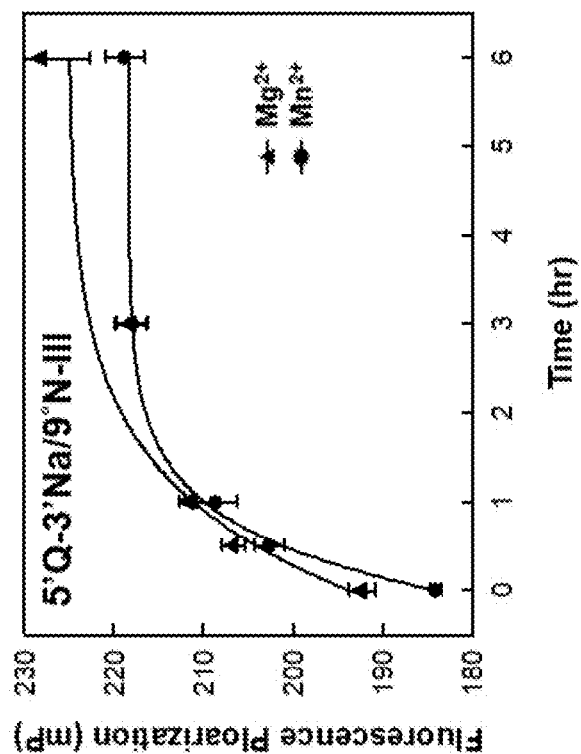
FIG. 3D shows a time-dependent increasing of FP activity of 5'Q-3'-Na catalyzed by 9° N-III in the presence of $Mn^{2+}$ and $Mg^{2+}$, respectively.
Figure 3C:
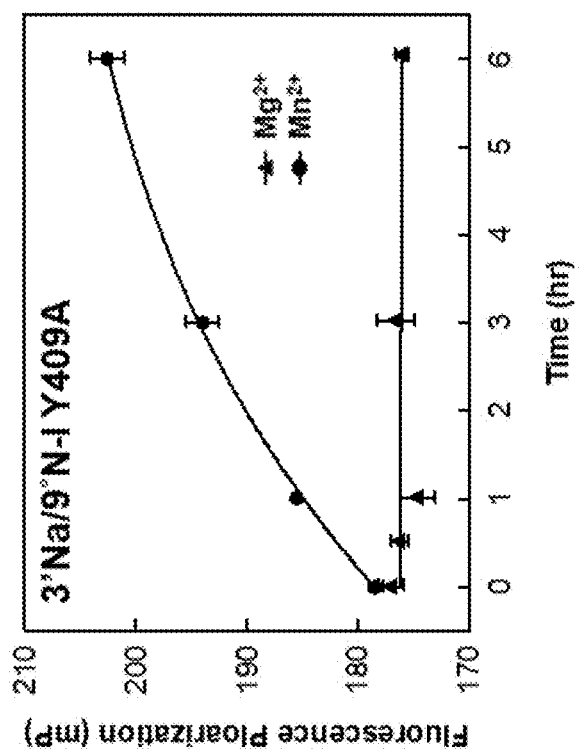
FIG. 3C shows a time-dependent increasing of FP activity of 3'-Na catalyzed by 9° N-I Y409A in the presence of $Mn^{2+}$ and $Mg^{2+}$, respectively.

Fluorescence Polarization (FP) Measurement of 3'-Modified Nucleotide After Incorporation into Primer Fluorescence polarization (FP) assays were conducted to characterize nucleotide transient-binding to 9° N DNA polymerase. As shown in FIG. 3A, significant FP signals of 3'-Na after incorporation were obtained from 9° N-I Y409A catalysis only in the presence of divalent ion $Mn^{2+}$. However, as shown in FIG. 3B, both $Mn^{2+}$ and $Mg^{2+}$ could mediate FP signal formation of 5'Q-3'-Na through the incorporation of 9° N-III. As shown in FIG. 3C and FIG. 3D, FP signals were obtained in both 3'-Na and 5'Q-3'-Na in a time-dependent manner (0-6 hours), in which FP reached to the maximal intensities at 6 hours. As a result, the increasing FP signals over time implied that the successful prolonging of extension products and accumulation of 3'-incorporated intermediates with fluorephore were occurred.

Polymerase End Point (PEP) Assay for 3'-Esterified Nucleotide Incorporation

Figure 4A:
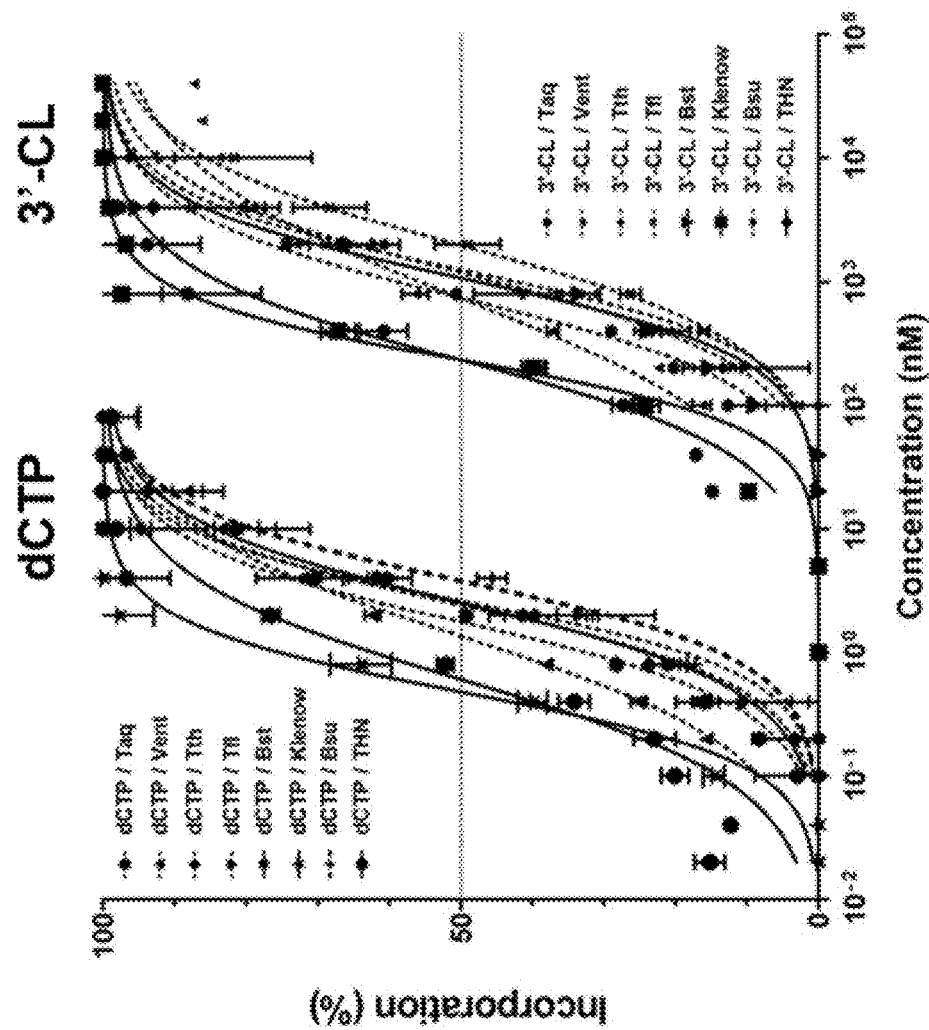
FIG. 4A shows polymerase end-point (PEP) discrimination curves and results for dCTP and 3'-CL catalyzed by eight DNA polymerases.
Figure 4C:
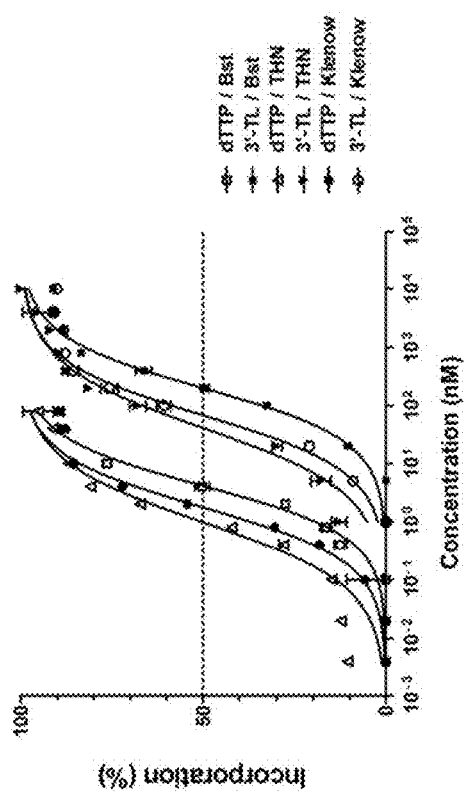
FIG. 4C shows PEP discrimination curves and results for dTTP and 3'-TL catalyzed by Bst-Lg, THN and Klenow.
Figure 4B:
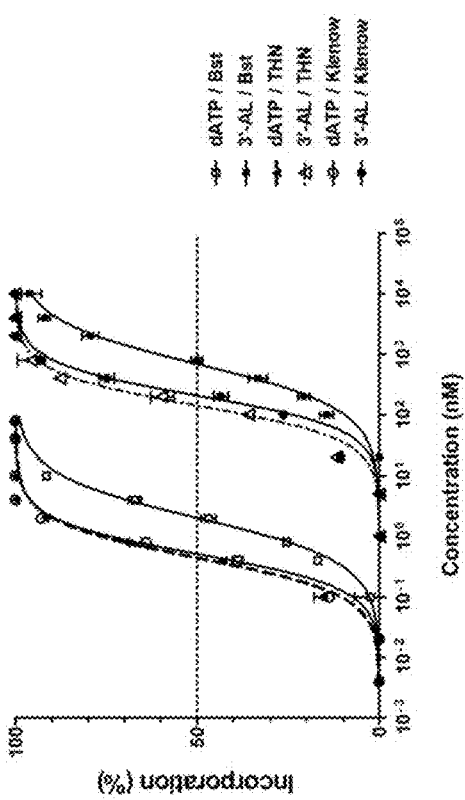
FIG. 4B shows PEP discrimination curves and results for dATP and 3'-AL catalyzed by Bst-Lg, THN and Klenow.
Figure 4E:
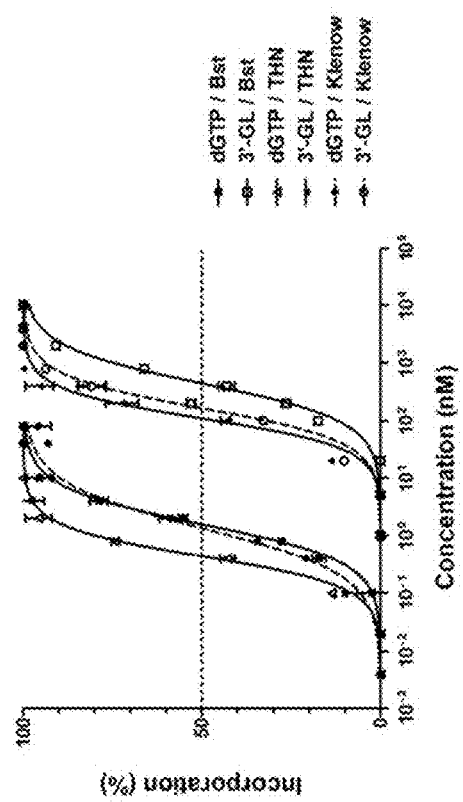
FIG. 4E shows PEP discrimination curves and results for dGTP and 3'-GL catalyzed by Bst-Lg, THN and Klenow.
Figure 4D:
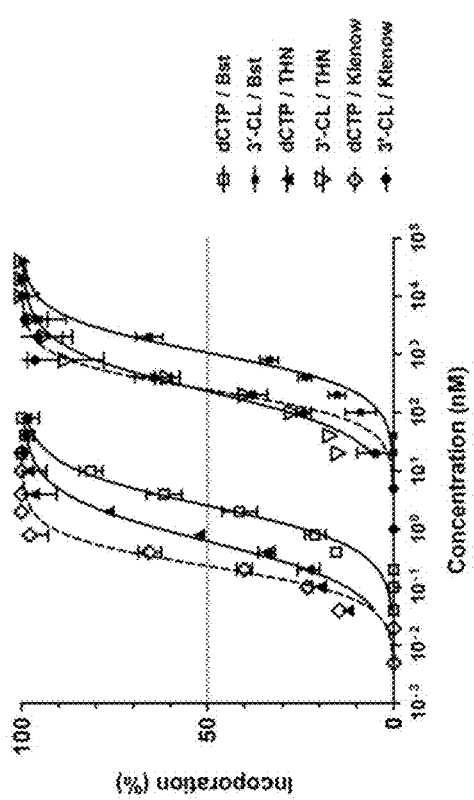
FIG. 4D shows PEP discrimination curves and results for dCTP and 3'-CL catalyzed by Bst-Lg, THN and Klenow.
Figure 5B:
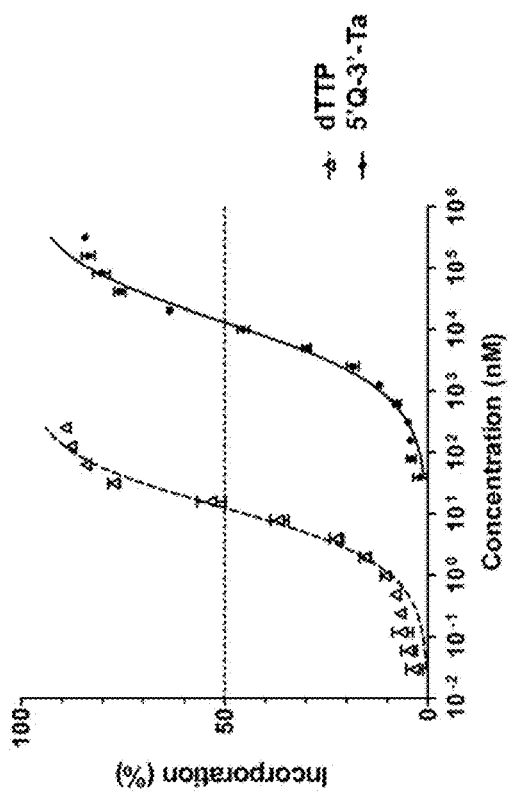
FIG. 5B shows PEP discrimination curves and results for dTTP and 5'Q-3'-Ta catalyzed by 9° N-III.
Figure 5A:
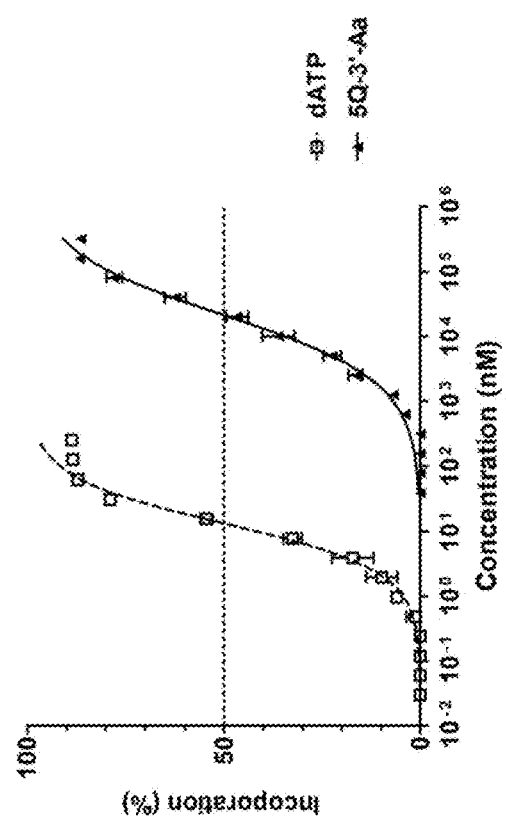
FIG. 5A shows PEP discrimination curves and results for dATP and 5'Q-3'-Aa catalyzed by 9° N-III.
Figure 5D:
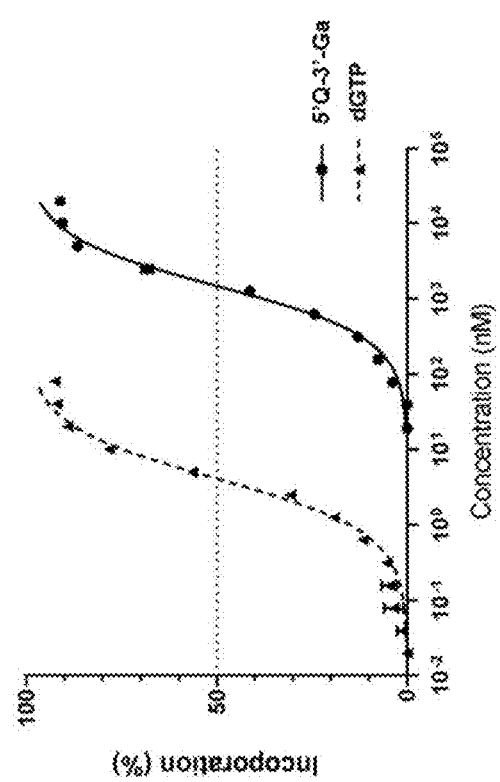
FIG. 5D shows PEP discrimination curves and results for dGTP and 5'Q-3'-Ga catalyzed by 9° N-III.
Figure 5C:
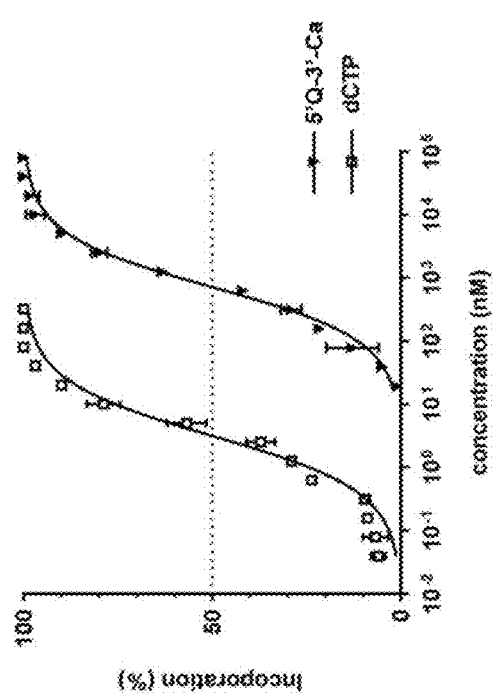
FIG. 5C shows PEP discrimination curves and results for dCTP and 5'Q-3'-Ca catalyzed by 9° N-III.

The incorporation efficiency of the 3' esterified compounds 3'-NL and 5'Q-3'-Na were determined using the quantitative PEP assay, which could be used for screening the modified compounds in a high-throughput manner. Accordingly, the end-point concentration, $IC_{50}$ value, of the respective nucleotide was calculated. As shown in FIG. 4A, dCTP and 3'-CL were estimated from eight DNA polymerases (including Taq, Vent, Tth, Tfl, Bst-Lg, Klenow, Bsu and THN), in which the titration of appropriate concentration range was made in each nucleotide. Both compounds were incorporated by all the polymerases examined, with $IC_{50}$ values ranging from 0.59 nM to 5.16 nM(dCTP) and 276.69 nM to 2087.36 nM (3'-CL), respectively. Among the eight DNA polymerases, THN and Klenow revealed preference for 3'-CL as many as 5-6 folds of incorporation efficiency over that of the others (see Table 3).

TABLE 3

$IC_{50}$ values of dCTP and 3'-CL estimated from eight DNA polymerases

| DNA polymerase | Average $IC_{50}$ ± SD | | Incorporation bias |
|---|---|---|---|
| | dCTP (nM) | 3'-CL (nM) | |
| Bst-Lg | 2.92 ± 0.34 | 1496.89 ± 24.49 | 511.23 |
| THN | 0.87 ± 0.04 | 300.65 ± 12.89 | 343.6 |
| Klenow | 0.59 ± 0.007 | 276.69 ± 9.17 | 468.96 |
| Taq | 2.31 ± 0.09 | 1037.94 ± 194.92 | 447.80 |
| Vent | 1.49 ± 0.02 | 796.45 ± 25.26 | 557.22 |
| Tth | 3.05 ± 0.17 | 1448.34 ± 67.62 | 474.14 |
| Tfl | 3.47 ± 0.55 | 1633.47 ± 85.37 | 470.34 |
| Bsu | 5.16 ± 0.22 | 2087.36 ± 245.61 | 404.25 |

As shown in FIGS. 4B, 4C, 4D and 4E, dNTP and 3'-NL were further estimated from the selected DNA polymerases Bst-Lg, THN and Klenow with appropriate concentration range for each nucleotide. For 3'-NL, THN and Klenow had better $IC_{50}$ than that of Bst-Lg, and the preference of incorporation efficiency for those modified nucleotides is in general 3'-TL>3'-GL>3'-AL>3'-CL (see Table 4).

TABLE 4

IC50 values of dNTP and 3'-NL estimated from Bst-Lg, THN and Klenow

| DNA polymerase | Average $IC_{50}$ ± SD | | Incorporation bias |
|---|---|---|---|
| | dATP (nM) | 3'-AL (nM) | |
| Bst-Lg | 2.545 ± 0.067 | 948.34 ± 70.29 | 372.54 |
| THN | 0.526 ± 0.008 | 167.77 ± 5.64 | 318.67 |
| Klenow | 0.589 ± 0.008 | 244.56 ± 5.05 | 415.10 |

TABLE 4-continued

IC50 values of dNTP and 3'-NL estimated from Bst-Lg, THN and Klenow

| DNA polymerase | Average $IC_{50}$ ± SD | | Incorporation bias |
|---|---|---|---|
| | dTTP (nM) | 3'-TL (nM) | |
| Bst-Lg | 4.03 ± 0.142 | 196.01 ± 3.98 | 48.63 |
| THN | 0.99 ± 0.012 | 64.22 ± 2.93 | 64.73 |
| Klenow | 1.78 ± 0.016 | 79.10 ± 2.13 | 44.34 |
| | dCTP (nM) | 3'-CL (nM) | |
| Bst-Lg | 2.928 ± 0.34 | 1496.89 ± 24.49 | 511.23 |
| THN | 0.875 ± 0.04 | 300.65 ± 12.89 | 343.6 |
| Klenow | 0.59 ± 0.007 | 276.69 ± 9.17 | 468.96 |
| | dGTP (nM) | 3'-GL (nM) | |
| Bst-Lg | 1.77 ± 0.038 | 541.13 ± 9.37 | 304.79 |
| THN | 0.509 ± 0.009 | 128.04 ± 6.41 | 251.55 |
| Klenow | 1.6 ± 0.083 | 198.59 ± 4.33 | 124.07 |

As shown in FIGS. 5A, 5B, 5C and 5D, dNTP and 5'Q-3'-Na were estimated from the recombinant 9° N-III DNA polymerase for incorporation efficiency with the titration of appropriate concentration range for each nucleotide. The incorporation efficiency ($IC_{50}$) of 5'Q-3'-Ca (875 nM) is in general better than those of 5'Q-3'-Ga (1689 nM), 5'Q-3'-Ta (12420 nM) and 5'Q-3'-Aa (24140 nM), resulting in the incorporation bias range of 202.08 to 1724.28 to their natural nucleotides, respectively (see Table 5).

TABLE 5

IC50 values of dNTP and 5'Q-3'-Na estimated from 9°N-III DNA polymerase

| DNA polymerase | Average $IC_{50}$ ± SD | | Incorporation bias |
|---|---|---|---|
| | dATP (nM) | 5'Q-3'-Aa (nM) | |
| 9°N-III | 14 ± 0.60 | 24140 ± 322 | 1724.28 |
| | dTTP (nM) | 5'Q-3'-Ta (nM) | |
| 9°N-III | 14.16 ± 1.63 | 12420 ± 550 | 877.11 |
| | dCTP (nM) | 5'Q-3'-Ca (nM) | |
| 9°N-III | 4.33 ± 0.45 | 875 ± 25 | 202.08 |
| | dGTP (nM) | 5'Q-3'-Ga (nM) | |
| 9°N-III | 4.72 ± 0.50 | 1689 ± 35 | 357.84 |

Pre-Steady State Kinetics of 9° N DNA Polymerase

To examine single-turnover kinetics of 9° N DNA polymerase on the 3'-esterified nucleotides, we performed pre-steady state kinetic experiments at 30° C. to determine the constants $k_{pol}$ and $K_d$ for dNTP, 3'-NL and 5'Q-3'-Na (see Table 6). For 3'-NL, $k_{pol}$ rate constants were 10.2 s$^{-1}$ (3'-AL), 14.6 s$^{-1}$ (3'-TL), 0.094 s$^{-1}$ (3'-CL) and 7.7 s$^{-1}$ (3'-GL), which are ~5- to 13-fold slower than their natural nucleotide counterparts, except for 3'-CL exhibits ~330-fold slower than dCTP. For 5'Q-3'-Na, $k_{pol}$ rate constants were 0.0209 s$^{-1}$ (5'Q-3'-Aa), 0.0359 s$^{-1}$ (5'Q-3'-Ta), 0.0185 s$^{-1}$ (5'Q-3'-Ca) and 0.1348 s$^{-1}$ (5'Q-3'-Ga), which are ~5- to 488-fold slower than their 3'-NL counterparts. The binding constants ($K_d$) for 5'Q-3'-Na are similar to their natural nucleotide counterparts and are ~3.9- to 19-fold higher than those for 3'-NL, indicating higher binding affinities of their quencher/fluorophore modification within the 9° N DNA polymerase active site.

TABLE 6

Pre-steady state kinetics of 9°N DNA polymerase with dNTP, 3'NL and 5'Q-3'-Na nucleotides

| Nucleotide | 9°N DNA Polymerase | $k_{pol}$ (s$^{-1}$) | $K_d$ (µM) | $k_{pol}/K_d$ (µM$^{-1}$s$^{-1}$) | $R^2$ |
|---|---|---|---|---|---|
| dATP | 9°N-I | 132.4 | 8.0 | 16.55 | 0.90 |
| dTTP | 9°N-I | 76.0 | 50.2 | 1.51 | 0.99 |
| dCTP | 9°N-I | 31.0 | 16.1 | 1.92 | 0.93 |
| dGTP | 9°N-I | 82.9 | 11.7 | 7.04 | 0.95 |
| 3'-AL | 9°N-I | 10.2 | 332.9 | 0.031 | 0.99 |
| 3'-TL | 9°N-I | 14.6 | 415.5 | 0.035 | 0.99 |
| 3'-CL | 9°N-I | 0.094 | 55.6 | 0.0017 | 0.95 |
| 3'-GL | 9°N-I | 7.7 | 274.6 | 0.0277 | 0.98 |
| 5'Q-3'-Aa | 9°N-III | 0.0209 | 17.5 | 0.00194 | 0.97 |
| 5'Q-3'-Ta | 9°N-III | 0.0359 | 33.2 | 0.00108 | 0.90 |
| 5'Q-3'-Ca | 9°N-III | 0.0185 | 14.3 | 0.00126 | 0.98 |
| 5'Q-3'-Ga | 9°N-III | 0.1348 | 29.3 | 0.00460 | 0.99 |

Figure 6:
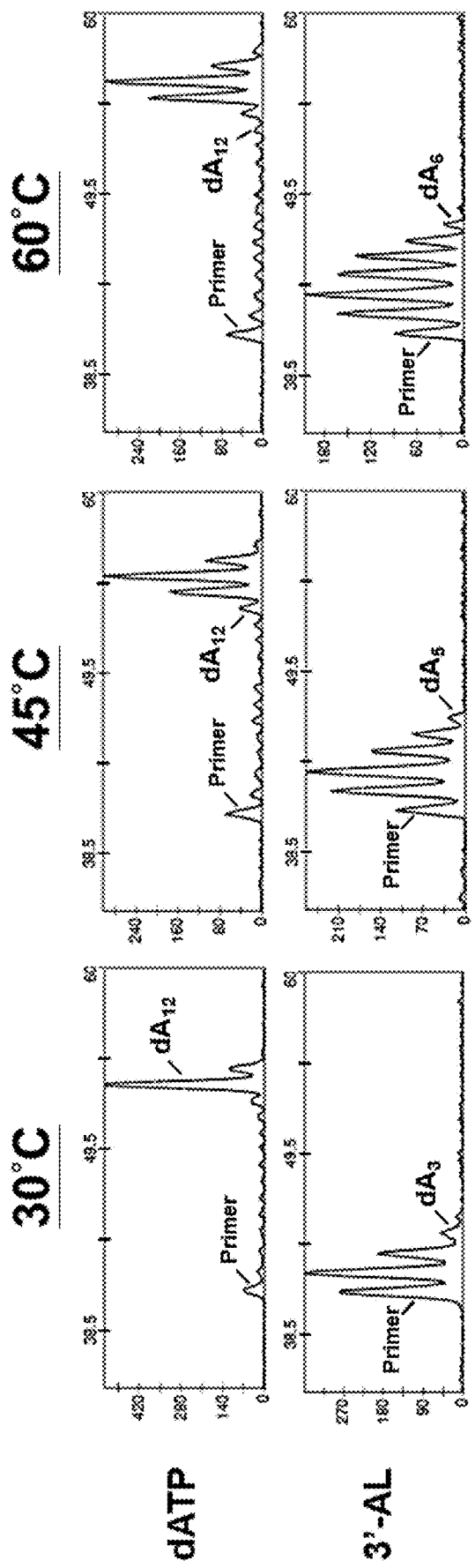
FIG. 6 shows primer extensions of dATP and 3'-AL with Bst-Lg on DNA template containing 12T homopolymeric sequence.

$k_{pol}$: nucleotide numbers to be incorporated by 9°N DNA Polymerase per second
$K_d$: binding affinity of nucleotide from 9°N DNA Polymerase Incorporation with Homopolymeric Template To investigate the incorporation performance of 3'-esterified nucleotide on homopolymer template strand, a primer extension of 3'-AL was performed with a template composed of twelve thymidine repeats (i.e. TTTTTTTTTTTT) using Bst-Lg DNA polymerase at different temperatures (e.g. 30, 45 and 60° C.) for 1 min and compared to its natural nucleotide counterpart (see FIG. 6). For 3'-AL, the extension products revealed a temperature-dependent increase with the numbers of dA repeats from three to six (i.e. $dA_3$ at 30° C., $dA_5$ at 45° C. and $dA_6$ at 60° C.), which are shorter than those of dATP with in general over twelve dA repeats ($dA_{12}$) in all conditions.

Elongation Activity of 3'-Modified Nucleotides

Figure 7B:
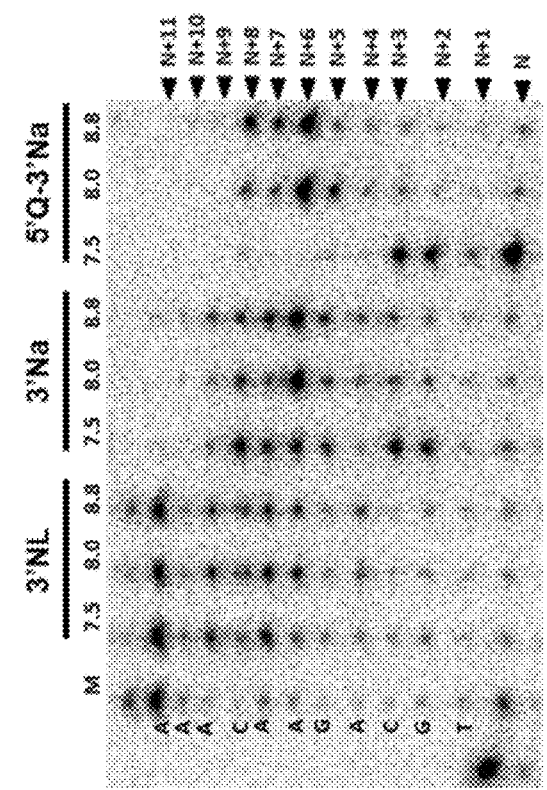
FIG. 7B shows DNA elongations of 3'-NL, 3'-Na and 5'Q-3'-Na nucleotides catalyzed by 9° N-III at pH 7.5, 8.0 and 8.8, respectively.
Figure 7A:
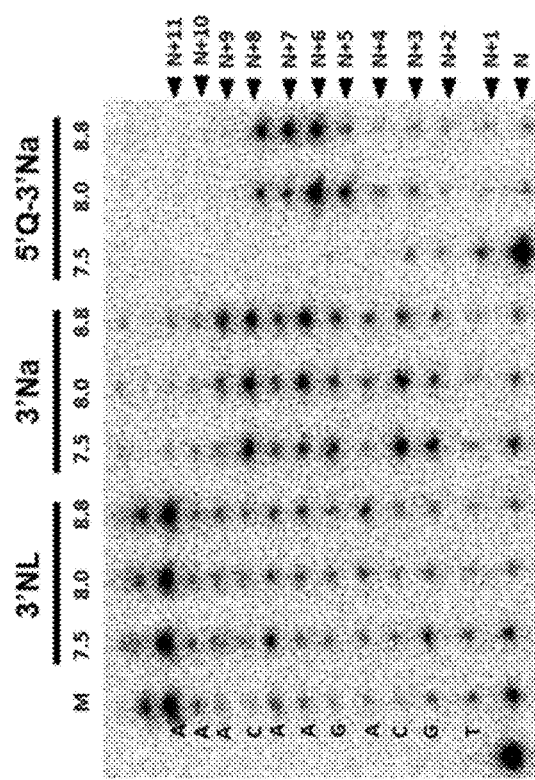
FIG. 7A shows DNA elongations of 3'-NL, 3'-Na and 5'Q-3'-Na nucleotides catalyzed by 9° N-I at pH 7.5, 8.0 and 8.8, respectively.
Figure 7C:
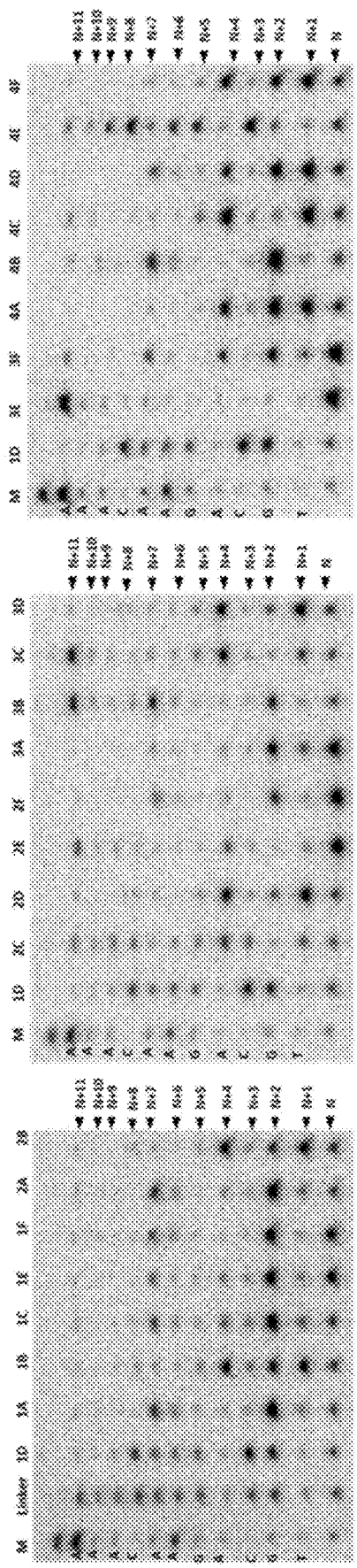
FIG. 7C shows DNA elongations of the combined 3'-Na-d nucleotides catalyzed by 9° N-I.
Figure 7D:
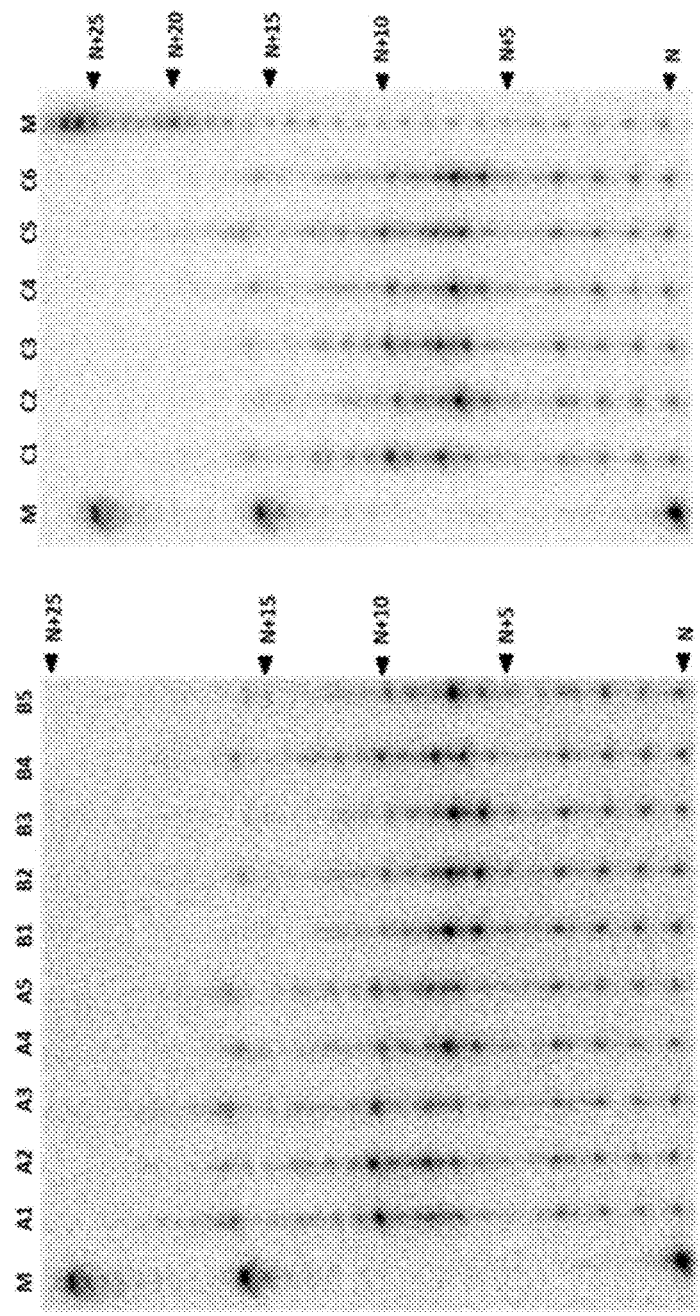
FIG. 7D shows DNA elongations of the combined 5'Q-3'-Na,d nucleotides catalyzed by 9° N-III.

To investigate DNA elongation performance of 3'-esterified nucleotide on random template strand, primer extensions of 3'-NL, 3'-Na and 5'Q-3'-Na were performed with 9° N DNA polymerase under different pH condition (e.g. pH 7.5, pH 8.0 and pH 8.8) (see FIG. 7A and FIG. 7B). In addition, the combination of different fluorophore connected to the natural nucleotides through a linker (i.e. 3'-Na-d, a total of 24 combinations as listed in Table 7) as well as the combination of different fluorophore/quencher (i.e. 5'Q-3'-Na,d, a total of 16 combinations as listed in Table 8) were also utilized for the primer extension (see FIG. 7C and FIG. 7D). The elongation activity for the respective 3'-esterified nucleotides was nucleotide—(i.e. 3'-NL>3'-Na>5'Q-3'-Na) and pH-dependent (i.e. pH 8.8>p8.0>7.5), and 9° N-I revealed better performance than that of 9° N-III on the incorporation of 3'-NL (see FIG. 7A) in contrast to 5'Q-3'-Na having better performance with 9° N-III than that of 9° N-I (see FIG. 7B). For 3'-Na-d, among the 24 combinations, there existed at least three of them exhibiting better elongation performance, such as combination 3B, 3C and 3E (see FIG. 7C and Table 7).

TABLE 7

List of the combinations of 3'-Na-d nucleotides for elongation assay

|  | A | T | C | G |
|---|---|---|---|---|
| Linker | 3'-AL | 3'-TL | 3'-CL | 3'-GL |
| 1D | 3'-Ad | 3'-Tb | 3'-Ca | 3'-Gc |
| 1A | 3'-Ad | 3'-Tc | 3'-Cb | 3'-Ga |
| 1B | 3'-Ad | 3'-Tc | 3'-Ca | 3'-Gb |
| 1C | 3'-Ad | 3'-Tb | 3'-Cc | 3'-Ga |
| 1E | 3'-Ad | 3'-Ta | 3'-Cc | 3'-Gb |
| 1F | 3'-Ad | 3'-Ta | 3'-Cb | 3'-Gc |
| 2A | 3'-Ac | 3'-Td | 3'-Cb | 3'-Ga |
| 2B | 3'-Ac | 3'-Td | 3'-Ca | 3'-Gb |
| 2C | 3'-Ac | 3'-Tb | 3'-Cd | 3'-Ga |
| 2D | 3'-Ac | 3'-Tb | 3'-Ca | 3'-Gd |
| 2E | 3'-Ac | 3'-Ta | 3'-Cd | 3'-Gb |
| 2F | 3'-Ac | 3'-Ta | 3'-Cb | 3'-Gd |
| 3A | 3'-Ab | 3'-Td | 3'-Cc | 3'-Ga |
| 3B | 3'-Ab | 3'-Td | 3'-Ca | 3'-Gc |
| 3C | 3'-Ab | 3'-Tc | 3'-Cd | 3'-Ga |
| 3D | 3'-Ab | 3'-Tc | 3'-Ca | 3'-Gd |
| 3E | 3'-Ab | 3'-Ta | 3'-Cd | 3'-Gc |
| 3F | 3'-Ab | 3'-Ta | 3'-Cc | 3'-Gd |
| 4A | 3'-Aa | 3'-Td | 3'-Cc | 3'-Gb |
| 4B | 3'-Aa | 3'-Td | 3'-Cb | 3'-Gc |
| 4C | 3'-Aa | 3'-Tc | 3'-Cd | 3'-Gb |
| 4D | 3'-Aa | 3'-Tc | 3'-Cb | 3'-Gd |
| 4E | 3'-Aa | 3'-Tb | 3'-Cd | 3'-Gc |
| 4F | 3'-Aa | 3'-Tb | 3'-Cc | 3'-Gd |

For 5'Q-3'-Na,d, some of the combinations exhibited better performance, such as combination A1, A3, A5 and C5 (see FIG. 7D and Table 8), suggesting the preference of fluorophore selection on the natural nucleotides for 9° N DNA polymerase activity.

TABLE 8

List of the combinations of 5'Q-3'-Na,d nucleotides for elongation assay

|  | A | T | C | G |
|---|---|---|---|---|
| A1 | 5'Q-3'-Aa | 5'Q-3'-Ta | 5'Q-3'-Ca | 5'Q-3'-Ga |
| A2 | 5'Q-3'-Ad | 5'Q-3'-Ta | 5'Q-3'-Ca | 5'Q-3'-Ga |
| A3 | 5'Q-3'-Aa | 5'Q-3'-Td | 5'Q-3'-Ca | 5'Q-3'-Ga |
| A4 | 5'Q-3'-Aa | 5'Q-3'-Ta | 5'Q-3'-Cd | 5'Q-3'-Ga |
| A5 | 5'Q-3'-Aa | 5'Q-3'-Ta | 5'Q-3'-Ca | 5'Q-3'-Gd |
| B1 | 5'Q-3'-Ad | 5'Q-3'-Td | 5'Q-3'-Cd | 5'Q-3'-Gd |
| B2 | 5'Q-3'-Ad | 5'Q-3'-Ta | 5'Q-3'-Cd | 5'Q-3'-Gd |
| B3 | 5'Q-3'-Ad | 5'Q-3'-Ta | 5'Q-3'-Cd | 5'Q-3'-Gd |
| B4 | 5'Q-3'-Ad | 5'Q-3'-Td | 5'Q-3'-Ca | 5'Q-3'-Gd |
| B5 | 5'Q-3'-Ad | 5'Q-3'-Td | 5'Q-3'-Cd | 5'Q-3'-Ga |
| C1 | 5'Q-3'-Ad | 5'Q-3'-Td | 5'Q-3'-Ca | 5'Q-3'-Ga |
| C2 | 5'Q-3'-Ad | 5'Q-3'-Ta | 5'Q-3'-Cd | 5'Q-3'-Ga |
| C3 | 5'Q-3'-Ad | 5'Q-3'-Ta | 5'Q-3'-Ca | 5'Q-3'-Gd |
| C4 | 5'Q-3'-Aa | 5'Q-3'-Td | 5'Q-3'-Cd | 5'Q-3'-Ga |
| C5 | 5'Q-3'-Aa | 5'Q-3'-Td | 5'Q-3'-Ca | 5'Q-3'-Gd |
| C6 | 5'Q-3'-Aa | 5'Q-3'-Ta | 5'Q-3'-Cd | 5'Q-3'-Gd |

The processivity of 9° N DNA polymerase on 3'-esterified nucleotide with longer DNA template (M13 bacteriophage 100 base-long) was also investigated by using capillary electrophoresis.

Figure 8A:
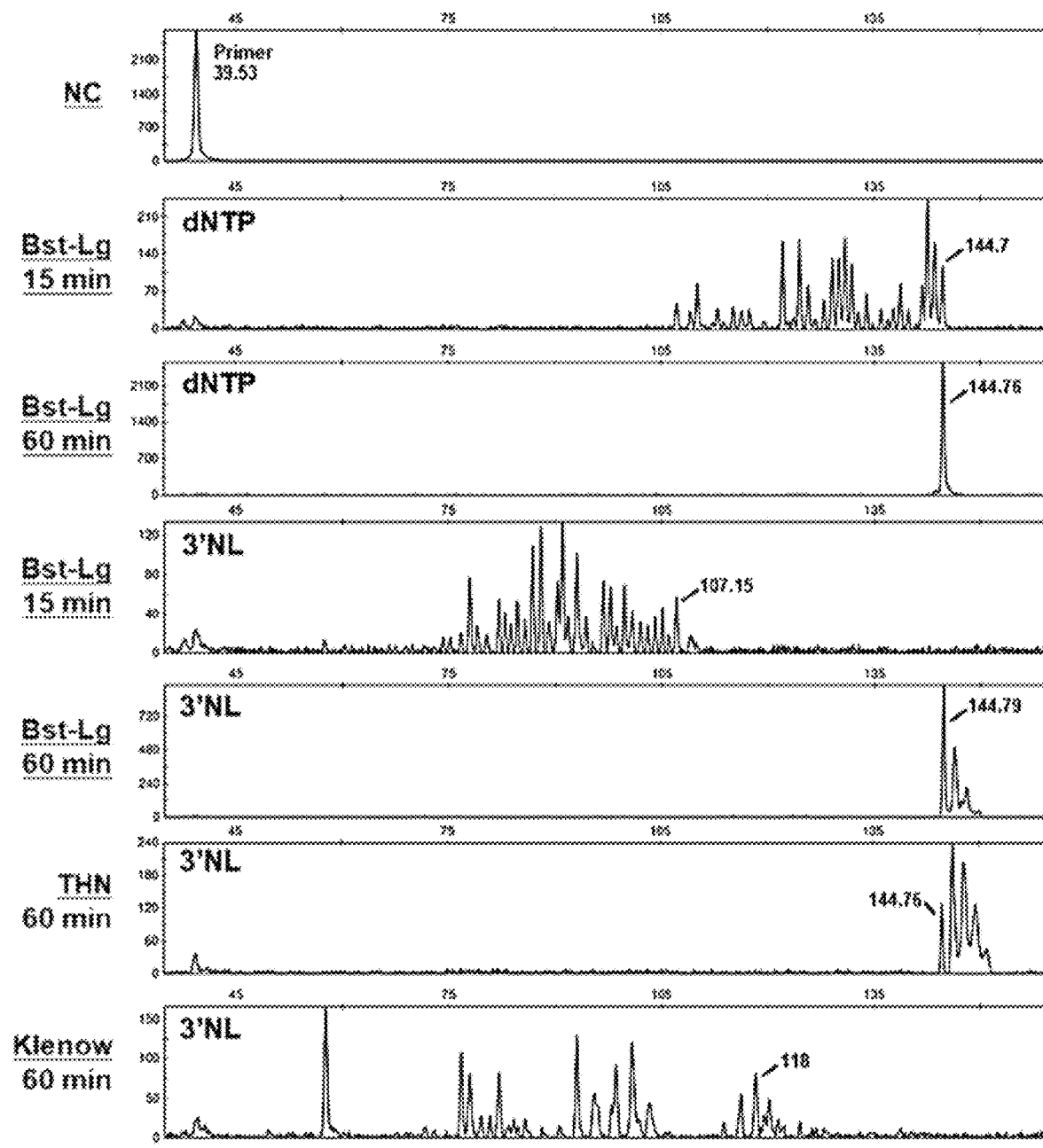
FIG. 8A shows DNA processivity of dNTP and 3'-NL catalyzed by DNA polymerase Bst-Lg, THN and Klenow.
Figure 8B:
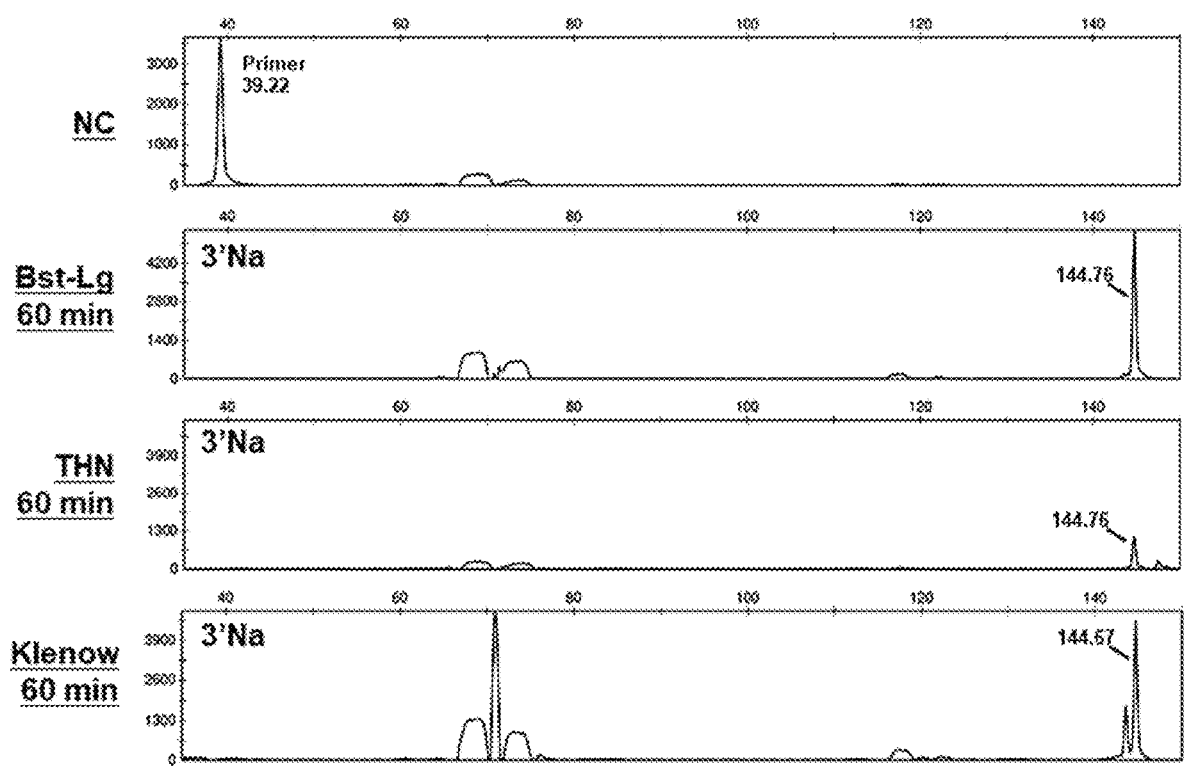
FIG. 8B shows DNA processivity of 3'-Na catalyzed by DNA polymerase Bst-Lg, THN and Klenow.
Figure 8C:
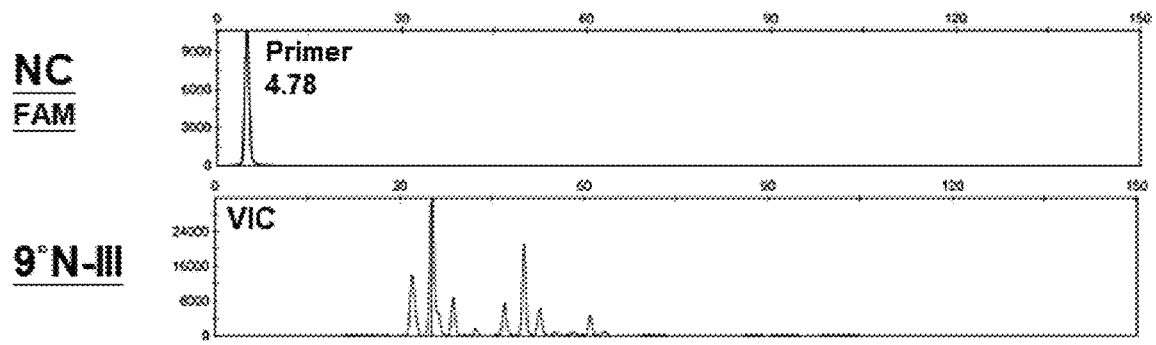
FIG. 8C shows DNA processivity of 5'Q-3'-Na catalyzed by 9° N-III.

As shown in FIG. 8A, time-dependent elongation of FAM-labeled primer was found from the natural and 3'-NL nucleotides with Bst-Lg DNA polymerase, in which the template position ranges from 107.15 (in 15 min) to 144.79 (in 60 min). Similar results were found in THN and Klenow with their template position positioned in 144.76 and 118, respectively. Moreover, as shown in FIG. 8B, the fully-extended products were found with 3'-Na catalyzed by DNA polymerase Bst-Lg (144.76), THN (144.76) and Klenow (144.67). Similar results were found with 5'Q-3'-Na catalyzed by 9° N-III DNA polymerase (see FIG. 8C).

Screening of 9° N-III with Enhanced Incorporation Activity

To improve the performance of 9° N-III DNA polymerase on 5'Q-3'-Na, a single-base incorporation assay was performed with the selected 9° N-III mutants by using capillary electrophoresis. The mutagenesis of 9° N-III was on two regions, including amino acid sites at nucleotide binding pocket (e.g. T267, I268, V282, E325, D404, R406, S407, S408, A409, V410, K477, D480, R484, L485, I486, K487, I488, N491, D540, T541, D542, G543, E580, G581, D598, E599, E600, K602, T604, T605, R606) and DNA binding domain (e.g. M244, G245, D246, R247, N269, L270, S347, S348, T349, N351, L352, E354, G382, G383, Y384, A385, G386, G387, Y388, V389, E391, P392, S492, Y494, G495, Y496, G498, A500, T514, Y538, V589, T590, K592, Y594, G607, L608, E609, W615, H663, E664, Q665, I666, T667, D672, Y673, K674, A675, T676, G677, H679, V680, V698, G708, R709, I710, G711, Y731, E734, N735, Q736, P739, A740, E742), capable of directly interacting with 3'-esterified nucleotide and DNA (the annealed template and primer), respectively.

Figure 9A:
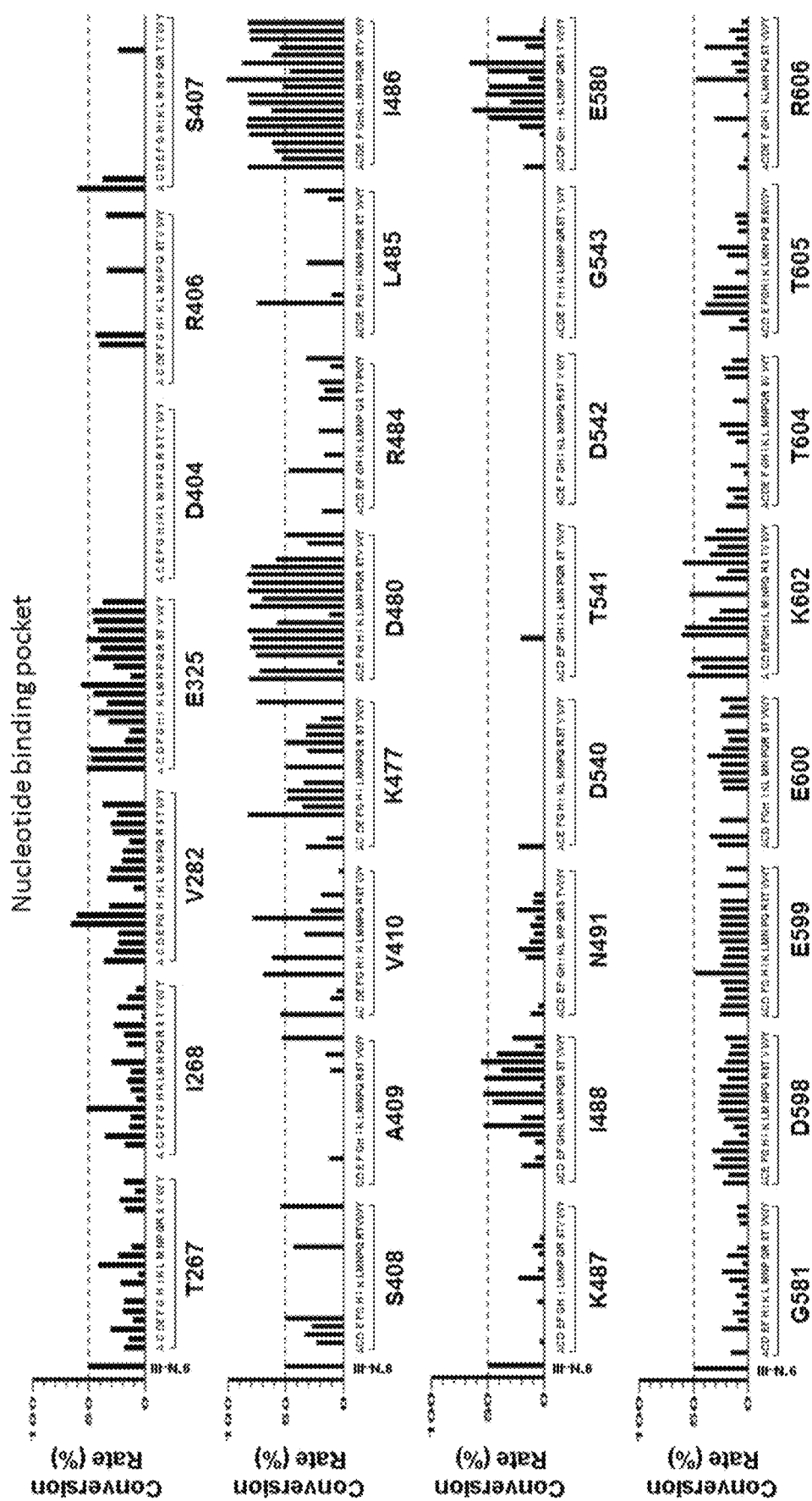
FIG. 9A shows a summary of the extension product conversion rate (C.R.) of 5'Q-3'-Ga catalyzed by the selected 9° N-III mutants of nucleotide binding pocket.
Figure 9B:
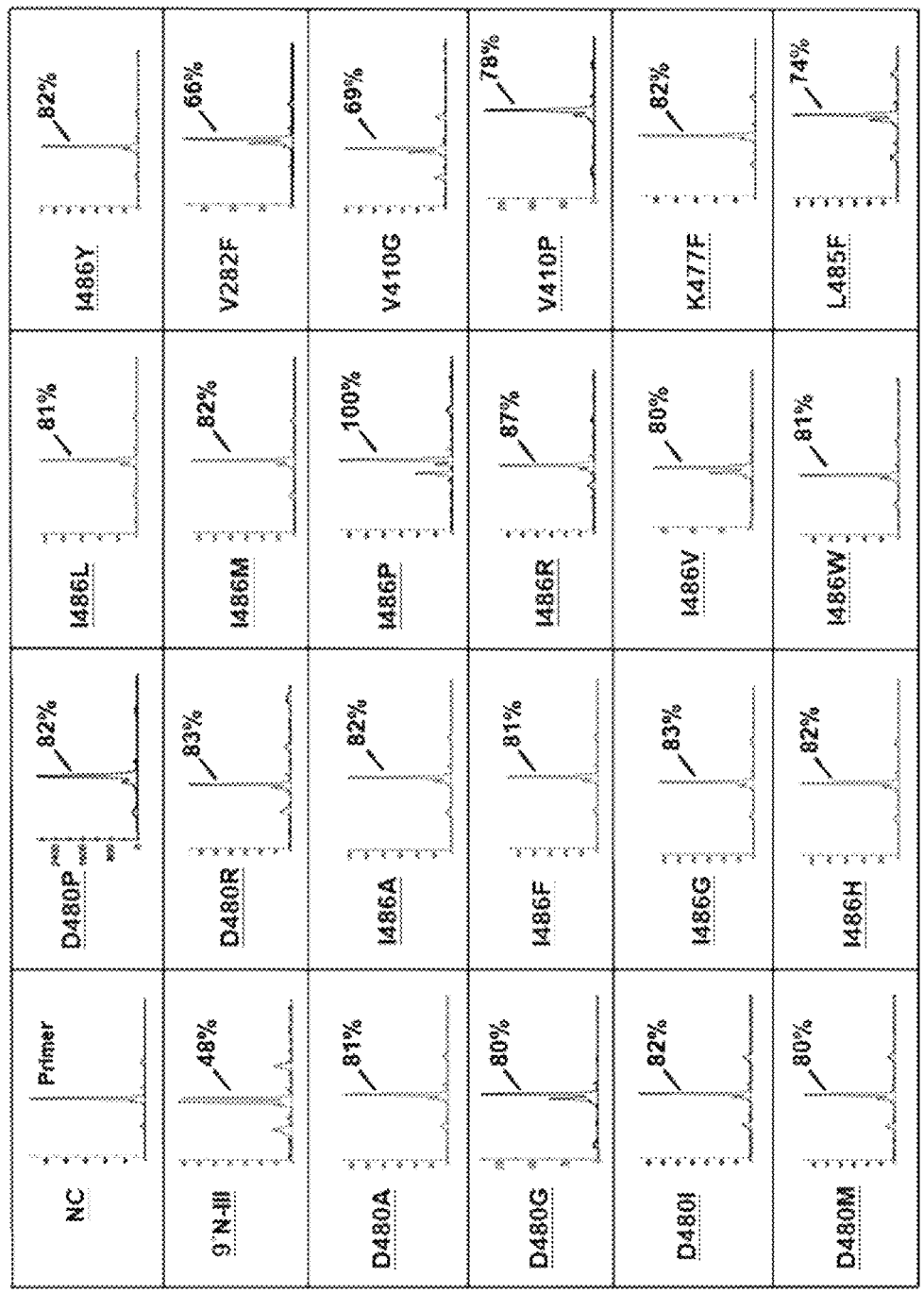
FIG. 9B shows a conversion of 5'Q-3'-Ga from 9° N-III mutants of nucleotide binding pocket analyzed by capillary electrophoresis.
Figure 9C:
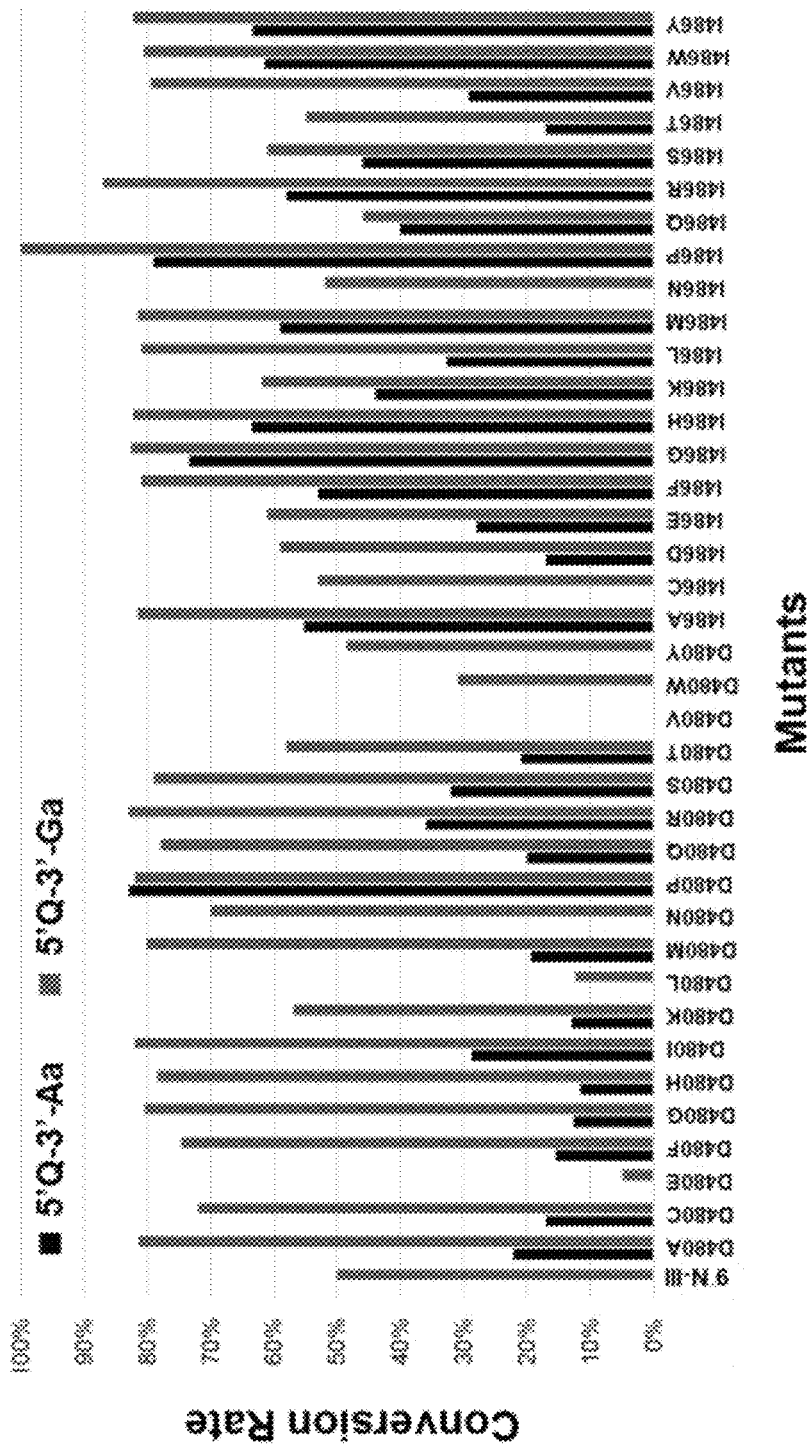
FIG. 9C shows a quantitative comparison of the conversion of both 5'Q-3'-Aa and 5'Q-3'-Ga nucleotides with the catalysis of 9° N-III D480 and I486 mutants.

For the selected sites of nucleotide binding pocket, the nineteen amino acids of the corresponding residue of 9° N-III were made by using typical site-directed mutagenesis. Among all, in the initial screening, at least twelve of the selected sites exhibiting higher incorporation activities than that of 9° N-III on 5'Q-3'-Ga (conversion rate (C.R.)>50%), including I268, V282, E325, S407, S408, A409, V410, K477, D480, L485, I486, and E580 (see FIG. 9A). Particularly, the increased incorporation products depicted as percentage of C.R. were found in V282F (66%), V410G (69%), V410P (78%), K477F (82%), D480A (81%), D480G (80%), D480I (82%), D480M (80%), D480P (82%), D480R (83%), L485F (74%), I486A (82%), I486F (81%), I486G (83%), I486H (82%), I486L (81%), I486M (82%), I486P (100%), I486R (87%), I486V (80%), I486W (81%), I486Y (82%) as compared to that of 9° N-III (48%) (see FIG. 9B). Moreover, the selected D480 and I486 mutants of 9° N-III were examined on the incorporation of 5'Q-3'-Aa, and most of the mutants exhibited increased incorporation products than that of 9° N-III with 0% C.R. (see FIG. 9C).

Figure 10A:
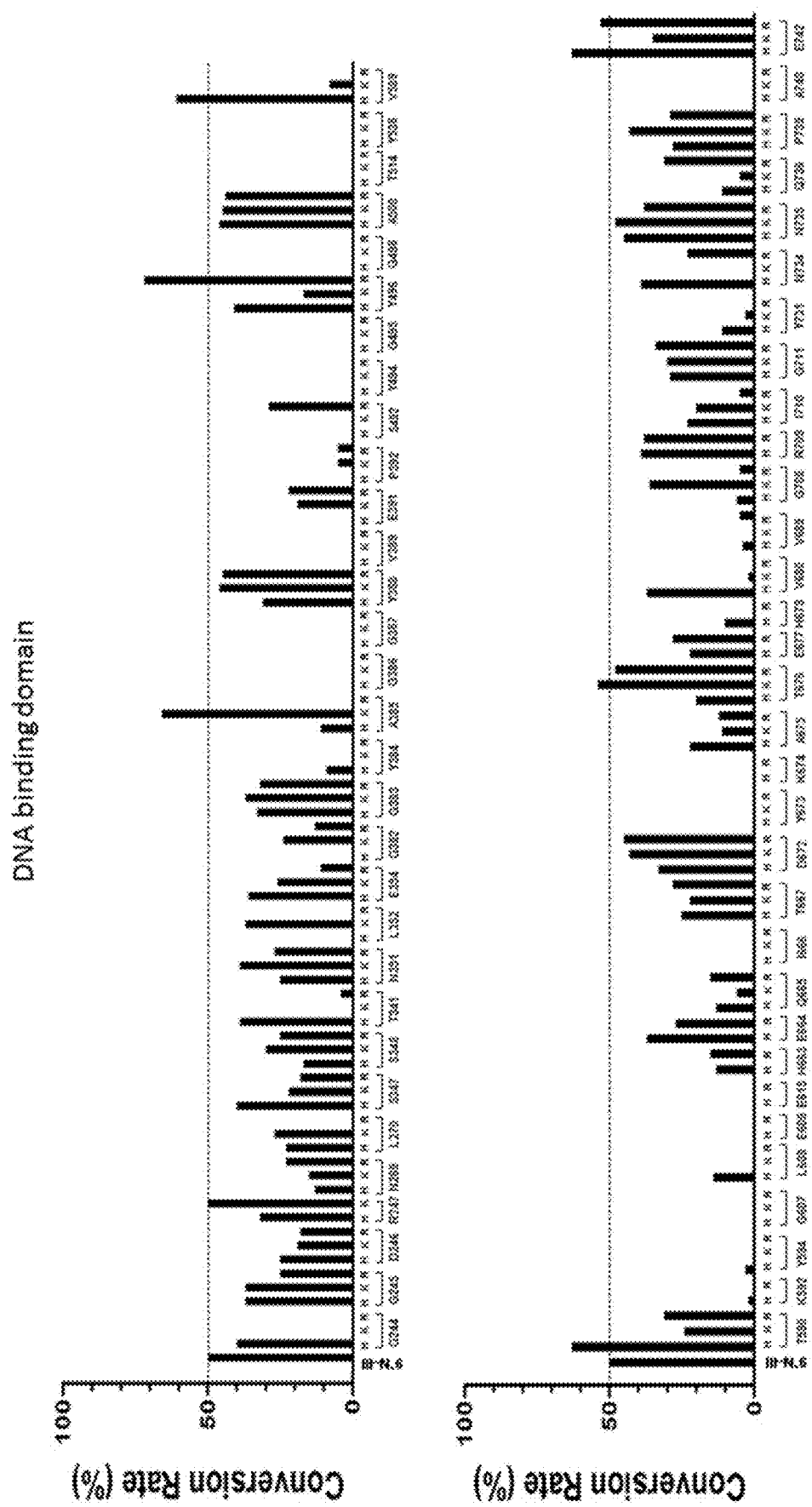
FIG. 10A shows a summary of the extension product conversion rate (C.R.) of 5'Q-3'-Ga catalyzed by the selected 9° N-III mutants of DNA binding domain.
Figure 10B:
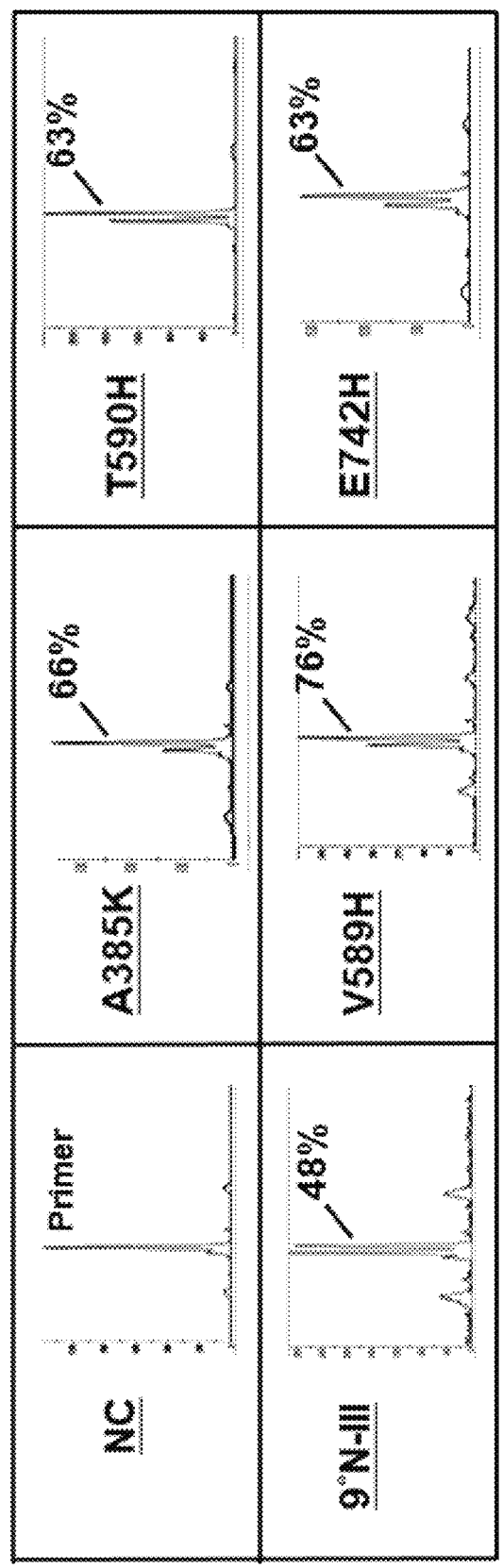
FIG. 10B shows a conversion of 5'Q-3'-Ga from 9° N-III mutants of DNA binding domain analyzed by capillary electrophoresis.

For the selected sites of DNA binding domain, the three amino acids (Lys, Arg and His) of the corresponding residue of 9° N-III were made by using typical site-directed mutagenesis. Among all, in the initial screening, six of the selected sites exhibiting higher incorporation activities than that of 9° N-III on 5'Q-3'-Ga (C.R.>50%), including R247, A385, V589, T590, T676, and E742 (see FIG. 10A). Particularly, the increased incorporation products were found in A385K (66%), V589H (76%), T590H (63%), and E742H (63%) as compared to that of 9° N-III (48%) (see FIG. 10B).

Figure 9D:
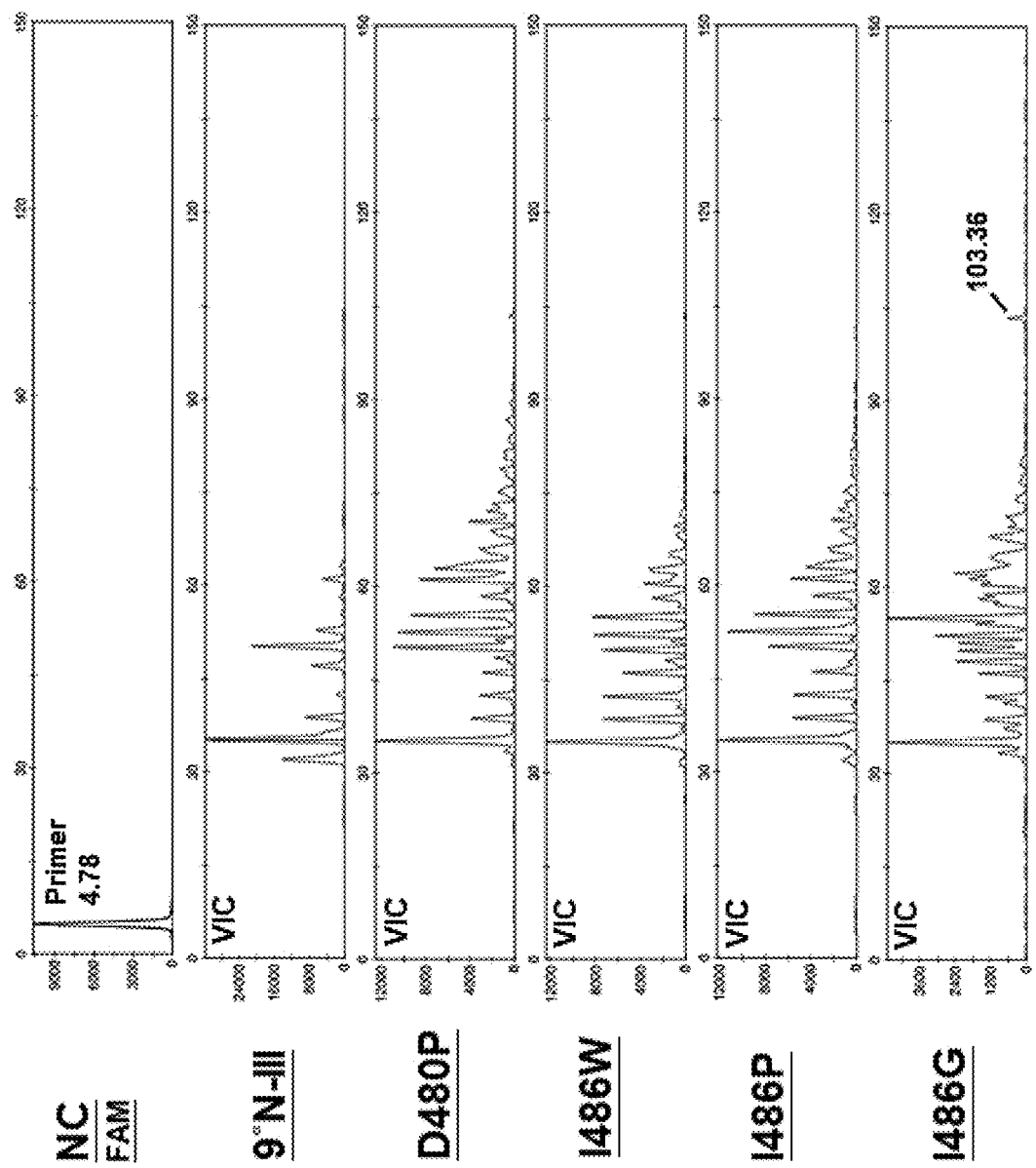
FIG. 9D shows DNA processivity of 5'Q-3'-Na catalyzed by the selected 9° N-III mutants of nucleotide binding pocket.
Figure 10C:
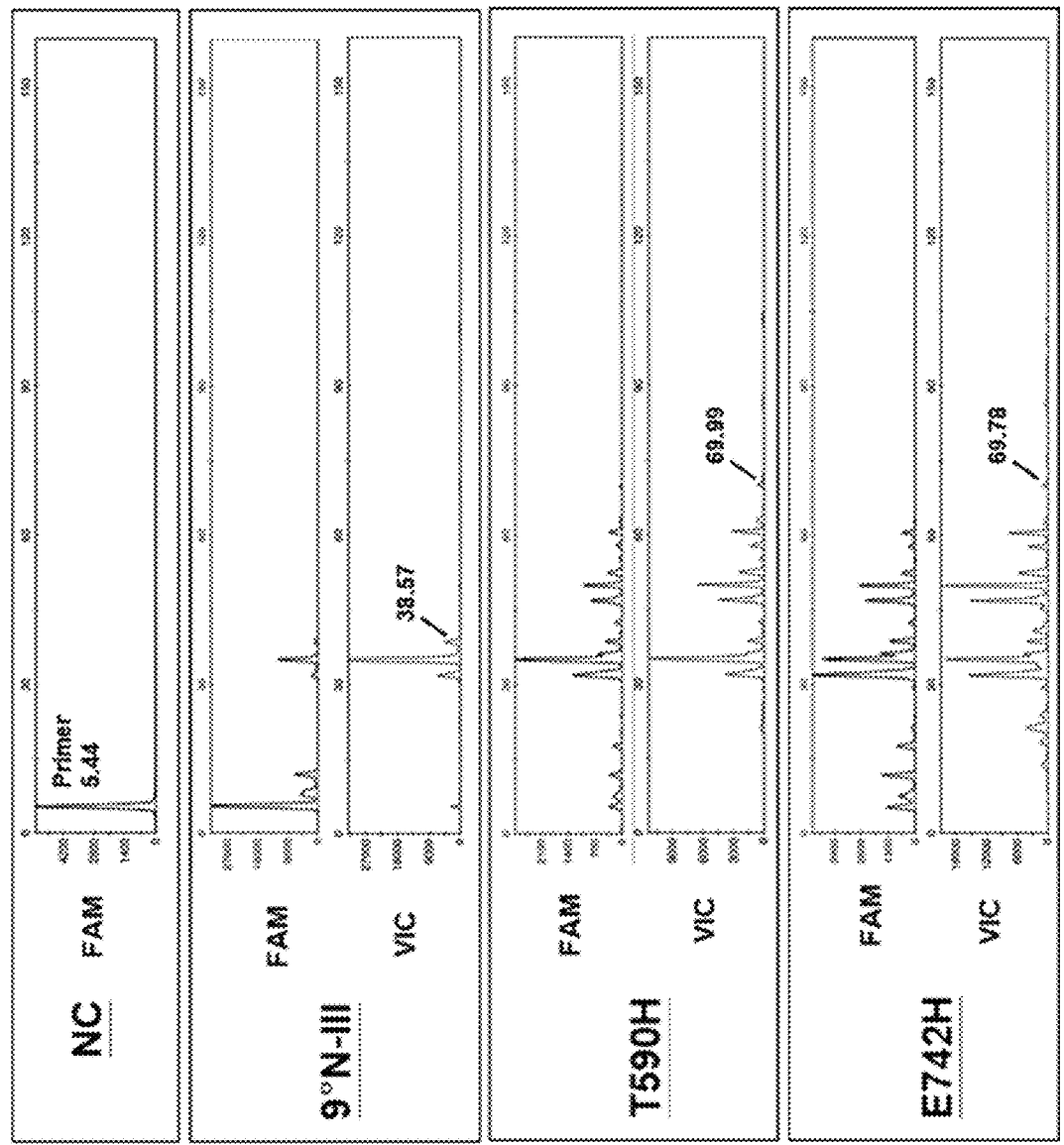
FIG. 10C shows DNA processivity of 5'Q-3'-Na catalyzed by the selected 9° N-III mutants of DNA binding domain

The processivity of 9° N-III on 5'Q-3'-Na with M13 bacteriophage 100 base-long template was also investigated by using capillary electrophoresis. The selected mutants of 9° N-III from the nucleotide binding pocket (D480P, I486G, I486P and I486W) and DNA binding domain (T590H and E742H) all exhibited increased template position over 60 with VIC signal (depicted as ATTO532 incorporation) (see FIG. 9D and FIG. 10C).

Figure 11:
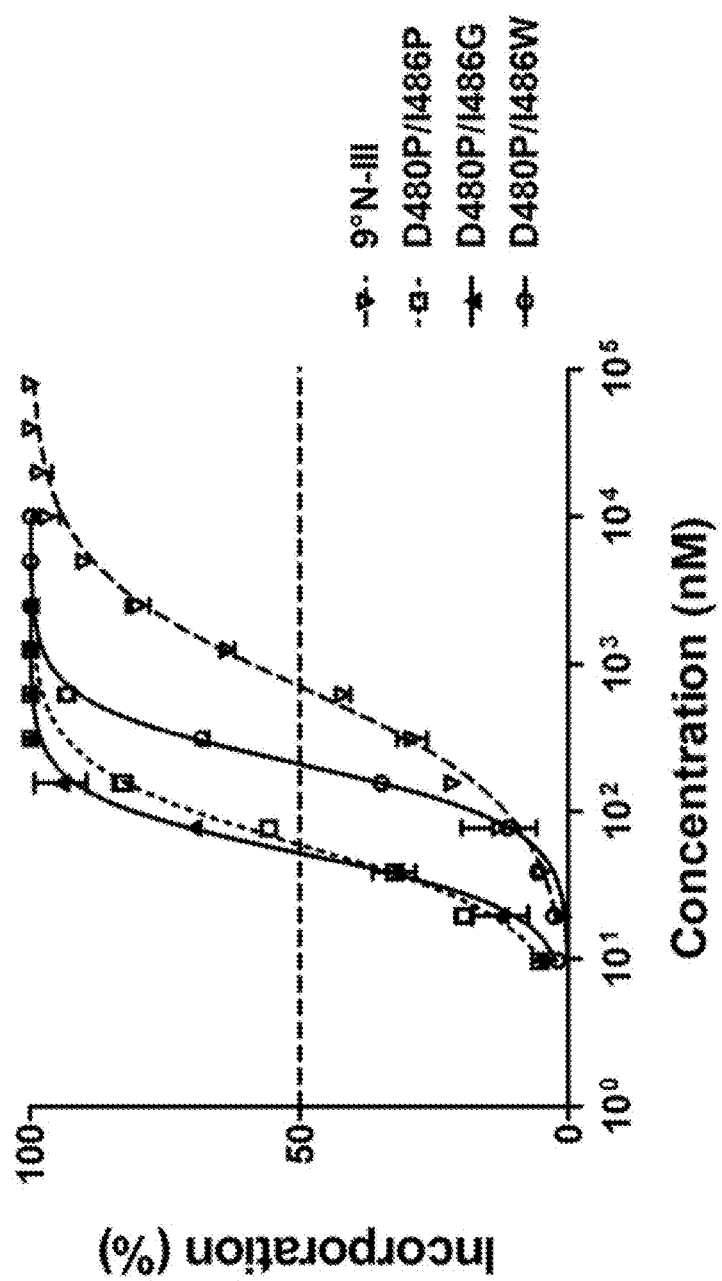
FIG. 11 shows PEP discrimination curves and results for 5'Q-3'-Ca catalyzed by the selected 9° N-III double mutants of nucleotide binding pocket

To further investigate whether the incorporation efficiency could be enhanced with the combination of the selected mutants, three double mutants from the nucleotide binding pocket of 9° N-III (D480P/I486G, D480P/I486P and D480P/I486W) were made for PEP and processivity assay. For 5'Q-3'-Ca, the $IC_{50}$ values were 57.6 nM (D480P/I486G), 74 nM (D480P/I486P) and 341.2 nM (D480P/I486W) in contrast to that of 875 nM (9° N-III) from PEP assay, indicating the incorporation efficiency was enhanced 2.5- to 15-fold (see FIG. 11 and Table 9).

TABLE 9

$IC_{50}$ values of 5'Q-3'-Ca estimated from the selected double mutants of 9°N-III DNA polymerase

| DNA polymerase | 5'Q-3'-Ca (nM) | Incorporation bias |
|---|---|---|
| 9°N-III | 875 ± 25 | — |
| D480P/I486G | 57.6 ± 14.2 | 0.066 |
| D480P/I486P | 74 ± 3.78 | 0.085 |
| D480P/I486W | 341.2 ± 16.5 | 0.39 |

Figure 12:
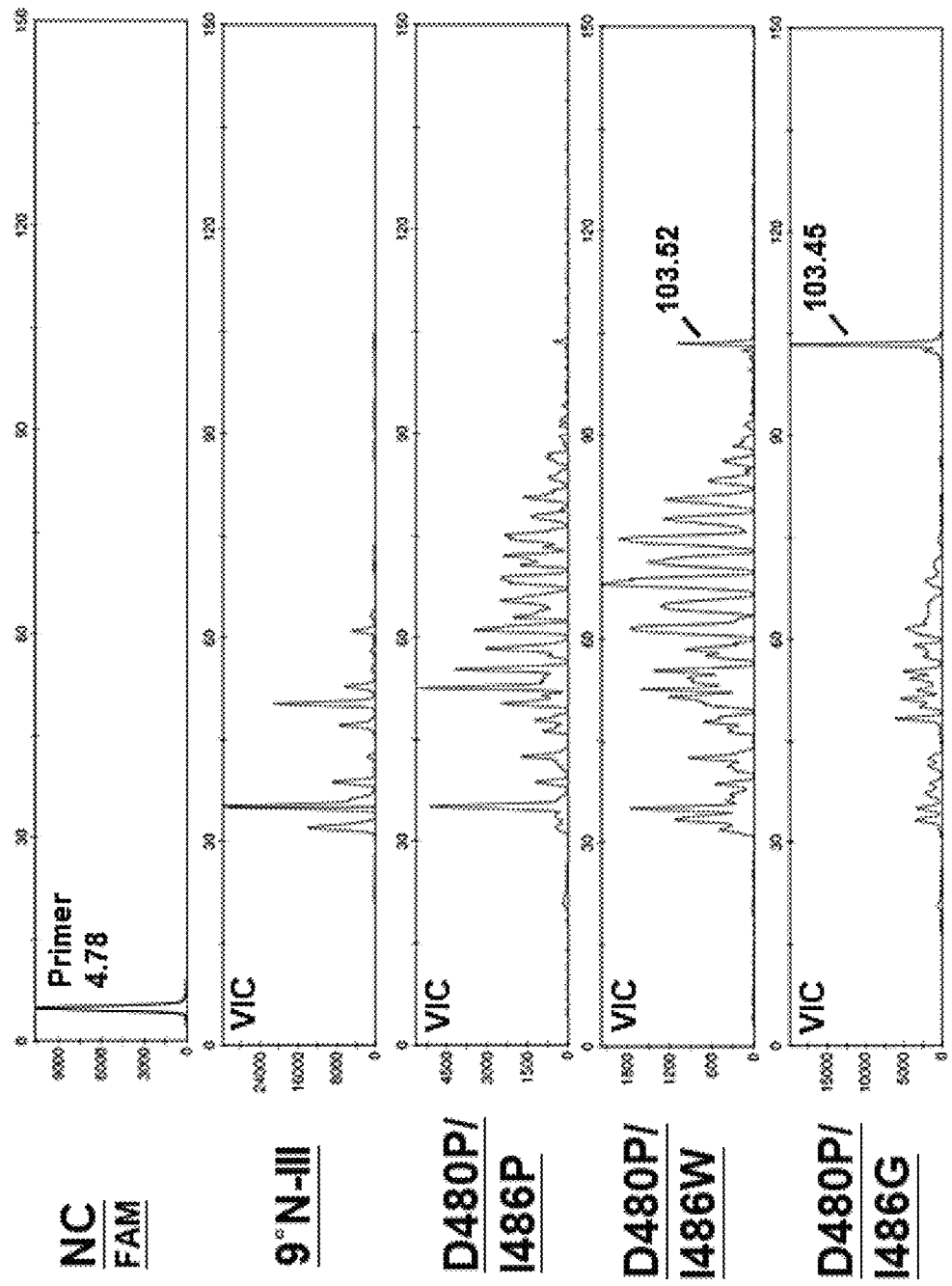
FIG. 12 shows DNA processivity of 5'Q-3'-Na catalyzed by the selected 9° N-III double mutants.

Moreover, the processivity of 9° N-III double mutants on 5'Q-3'-Na with M13 bacteriophage 100 base-long template was performed by using capillary electrophoresis. The three double mutants all exhibited increased template position over 100 with VIC signal (depicted as ATTO532 incorporation) (see FIG. 12). Similar results were found in $KOD^{exo-}$ and its D480 and I486 mutants, in which the conversion of 5'Q-3'-Ga was higher in D480H (84%), D480N (83%), D480W (77%) and I486G (78%) than that of $KOD^{exo-}$ (37%) after screening, and the processivity generally increased to over 100 by capillary electrophoresis.

In summary, there is provided a composition comprising family A and B DNA polymerases as well as 3'-esterified nucleotides, and demonstrate the 3' editing activity of 9° N DNA polymerase with MALDI-TOF MS and X-ray crystallography. The elongation activity of the 3'-esterified nucleotides in a sequential manner with fluorescence is further demonstrated by using fluorescence polarization and capillary electrophoresis. Furthermore, the activity of 9° N DNA polymerase on 3'-esterified nucleotide could be enhanced by the selected mutants of the nucleotide binding pocket and DNA binding domain. These results suggest the potential applications of said composition in DNA synthesis and sequencing with or without fluorescence detection.

What is claimed is:

1. A recombinant DNA polymerase having at least 99% sequence homology with the 9° N-III DNA polymerase of SEQ ID NO: 3 and the recombinant DNA polymerase comprises one or two mutations at the position corresponding to the amino acid residue 480 and 486 of the 9° N-III DNA polymerase of SEQ ID NO: 3.

2. The recombinant DNA polymerase of claim 1, wherein the mutation at the amino acid residue 480 is D480A, D480C, D480F, D480G, D480H, D480I, D480M, D480N, D480P, D480Q, D480R or D480S.

3. The recombinant DNA polymerase of claim 1, wherein the mutation at the amino acid residue 486 is I486A, I486F, I486G, I486H, I486L, I486M, I486P, I486R, I486V, I486W or I486Y.

4. The recombinant DNA polymerase of claim 1, wherein the recombinant DNA polymerase incorporates 3'-esterified nucleotide analogue in a template-dependent manner into a nascent strand, and the 3'-esterified nucleotide analogue is 3'-esterified nucleotide, 3'-ester-dye analogue or 3'-ester-dye analogue with quencher linked to phosphate group (3'-ester-dye/5'-Q).

5. The recombinant DNA polymerase of claim 4, wherein the 3'-ester-dye/5'-Q has the following formula (I):

wherein m is an integer and 1≤m≤10, L represents the linker group;

Rm and Rm+1 vary as m varies, and when m is larger than 1, Rm refers to a set of functional groups ranging from R1 to Rm, each of Rm may represent independently hydrogen (H) or a functional group consisting of a linker group Lm and a Fm, while Rm+1 may represent hydrogen (H) or a functional group consisting of a linker group Lm+1 and the Fm+1; the F, Fm or Fm+1 is independently a fluorescent dye or a quencher; the linker group Lm or Lm+1 is independently selected from alkyl, alkenyl, alkynyl, aryl, heteroaryl, heterocyclyl, polyethylene glycol, ester, amino, sulfonyl, or a combination thereof;

B represents a base selected from adenine, cytosine, guanine, thymine, uracil, hypoxanthine or 5-methylcytosine;

Z is independently selected from hydrogen, hydroxyl, thiol, halogen, or amino group; and Y in Formula I represents oxygen (O) or sulfur (S).

* * * * *

SEQUENCE LISTING

<160> NUMBER OF SEQ ID NOS: 15

<210> SEQ ID NO 1
<211> LENGTH: 775
<212> TYPE: PRT
<213> ORGANISM: Thermococcus sp. 9 degrees N-7
<220> FEATURE:
<221> NAME/KEY: misc_feature
<223> OTHER INFORMATION: 9 degrees N DNA polymerase

<400> SEQUENCE: 1

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
        180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
        405                 410                 415
```

```
Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
            485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 2
<211> LENGTH: 775
<212> TYPE: PRT
<213> ORGANISM: Thermococcus sp. 9 degrees N-7
<220> FEATURE:
<221> NAME/KEY: misc_feature
<223> OTHER INFORMATION: 9 degrees N-I DNA polymerase

<400> SEQUENCE: 2
```

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Ala Ile Ala Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415
```

```
Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
770                 775
```

<210> SEQ ID NO 3
<211> LENGTH: 775
<212> TYPE: PRT
<213> ORGANISM: Thermococcus sp. 9 degrees N-7
<220> FEATURE:
<221> NAME/KEY: misc_feature
<223> OTHER INFORMATION: 9 degrees N-III DNA polymerase

<400> SEQUENCE: 3

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ser Ala Val Ser Ile Ile Ile Thr His
                405                 410                 415
```

```
Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
            450                 455                 460

Arg Lys Met Lys Ala Thr Val Asp Pro Leu Glu Lys Lys Leu Leu Asp
465                 470                 475                 480

Tyr Arg Gln Arg Leu Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 4
<211> LENGTH: 774
<212> TYPE: PRT
<213> ORGANISM: Thermococcus kodakarensis kod1
<220> FEATURE:
<221> NAME/KEY: misc_feature
<223> OTHER INFORMATION: KOD1 DNA polymerase

<400> SEQUENCE: 4
```

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
        50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Asp Ile Glu Thr
        130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
        290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
        370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415
```

```
Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
        530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770
```

<210> SEQ ID NO 5
<211> LENGTH: 774
<212> TYPE: PRT
<213> ORGANISM: Thermococcus kodakarensis kod1
<220> FEATURE:
<221> NAME/KEY: misc_feature
<223> OTHER INFORMATION: KODexo- DNA polymerase

<400> SEQUENCE: 5

```
Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
            115                 120                 125

Met Glu Gly Asp Glu Glu Leu Lys Met Leu Ala Phe Ala Ile Ala Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
            275                 280                 285

Lys Val Tyr Ala Glu Glu Ile Thr Thr Ala Trp Glu Thr Gly Glu Asn
            290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Lys Glu Leu Ala Arg Arg Arg Gln Ser Tyr
            370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415
```

```
Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 6
<211> LENGTH: 2328
<212> TYPE: DNA
<213> ORGANISM: Thermococcus sp. 9 degrees N-7
<220> FEATURE:
<221> NAME/KEY: misc_feature
<223> OTHER INFORMATION: 9 degrees N-I DNA polymerase

<400> SEQUENCE: 6
```

```
atgattctgg atacggacta cattacggaa aacggcaaac cggttattcg tgtgttcaaa    60
aaggaaaacg gcgaatttaa gatcgaatat gatcgtacct ttgaaccgta tttctacgcg   120
ctgctgaaag atgacagtgc catcgaagac gtgaaaaagg ttaccgcaaa acgtcatggc   180
acggtggtta aagtgaagcg tgctgaaaaa gttcagaaaa agtttctggg tcgtccgatt   240
gaagtttgga aactgtactt caaccatccg caagatgtcc cggcaatccg cgaccgtatt   300
cgtgctcacc cggcggtcgt ggatatctat gaatacgaca ttccgtttgc gaagcgctat   360
ctgatcgata aaggcctgat tccgatggaa ggtgacgaag aactgaccat gctggcattt   420
gctattgcga cgctgtatca cgaaggcgaa gaatttggca ccggtccgat cctgatgatt   480
tcatacgccg atggttcgga agcacgtgtt atcacctgga aaagattga tctgccgtat   540
gtggacgttg tcagcacgga aaaggaaatg atcaaacgct tcctgcgtgt ggttcgtgaa   600
aaggatccgg acgtgctgat tacctataac ggcgataatt ttgacttcgc ctacctgaaa   660
aagcgttgcg aagaactggg tatcaaattt acgctgggcc gcgatggtag cgaaccgaaa   720
attcagcgca tgggcgaccg ttttgcagtc gaagtgaaag gtcgcatcca tttcgatctg   780
tacccggtta tccgtcgcac cattaacctg ccgacctata cgctggaagc tgtctacgaa   840
gcggtgttcg gcaaaccgaa ggaaaaagtg tatgcagaag aaattgccca ggcttgggaa   900
tcaggcgaag gtctgaaacg cgtggcacgt tattcgatgg aagatgctaa agttacgtac   960
gaactgggtc gcgaattttt cccgatggaa gcgcagctga gccgtctgat tggccaaagc  1020
ctgtgggatg tttctcgcag ctctaccggt aacctggtcg aatggtttct gctgcgcaag  1080
gcgtataaac gtaacgaact ggccccgaat aaaccggatg aacgtgaact ggcacgtcgc  1140
cgtggcggtt atgctggcgg ttacgttaaa gaaccggaac gtggtctgtg gataatatc  1200
gtgtatctgg acttccgcag tctgtacccg tccattatca ttacccataa cgttagtccg  1260
gatacgctga atcgcgaagg ctgcaaagaa tatgacgttg cgccggaagt cggtcacaag  1320
ttttgtaaag attttccggg cttcattccg tccctgctgg gtgacctgct ggaagaacgc  1380
cagaagatca agcgtaagat gaaagccacc gtggatccgc tggaaaagaa actgctggac  1440
tatcgccaac gtctgatcaa aattctggcg aacagctttt atggctatta cggttacgcc  1500
aaggcacgct ggtattgcaa agaatgtgcc gaatctgtga ccgcatgggg ccgcgaatac  1560
attgaaatgg tgatccgtga actggaagaa agttcggtt caaggttct gtatgcggat  1620
accgacggcc tgcatgccac gatcccgggt gctgatgcgg aaaccgtgaa aagaaagcg  1680
aaggaatttc tgaagtacat caacccgaag ctgccgggcc tgctggaact ggaatatgaa  1740
ggcttttacg tccgtggctt tttcgtgacg aagaaaaagt atgcggttat cgatgaagaa  1800
ggcaaaatta ccacgcgcgg tctggaaatc gtgcgccgtg actggtcaga aattgctaaa  1860
gaaacccagg cgcgtgtcct ggaagccatc ctgaaacacg tgatgtgga agaagcggtc  1920
cgcattgtga agaagttac ggaaaagctg tcgaaatatg aagtcccgcc ggaaaaactg  1980
gtgatccatg aacaaattac ccgcgatctg cgtgactaca agcaacggg tccgcacgtt  2040
gcagtcgcaa agcgtctggc agcacgtggt gtgaaaattc gtccgggcac cgttatcagt  2100
tatattgtcc tgaaaggctc cggtcgcatc ggtgatcgtg ccattccggc agatgaattt  2160
gacccgacga acaccgcta tgacgccgaa tattacatcg aaaatcaggt gctgccggca  2220
gttgaacgca ttctgaaggc ttttggctac cgtaaagaag atctgcgcta tcaaaaaacc  2280
aagcaagtcg gtctgggtgc gtggctgaaa gtcaagggca aaaaataa              2328
```

<210> SEQ ID NO 7
<211> LENGTH: 2328
<212> TYPE: DNA
<213> ORGANISM: Thermococcus sp. 9 degrees N-7
<220> FEATURE:
<221> NAME/KEY: misc_feature
<223> OTHER INFORMATION: 9 degrees N-III DNA polymerase

<400> SEQUENCE: 7

| | | | | | |
|---|---|---|---|---|---|
| atgattctgg | atacggacta | cattacggaa | aacggcaaac | cggttattcg tgtgttcaaa | 60 |
| aaggaaaacg | gcgaatttaa | gatcgaatat | gatcgtacct | tgaaccgta tttctacgcg | 120 |
| ctgctgaaag | atgacagtgc | catcgaagac | gtgaaaaagg | ttaccgcaaa acgtcatggc | 180 |
| acggtggtta | agtgaagcg | tgctgaaaaa | gttcagaaaa | agtttctggg tcgtccgatt | 240 |
| gaagtttgga | aactgtactt | caaccatccg | caagatgtcc | cggcaatccg cgaccgtatt | 300 |
| cgtgctcacc | cggcggtcgt | ggatatctat | gaatacgaca | ttccgtttgc gaagcgctat | 360 |
| ctgatcgata | aaggcctgat | tccgatggaa | ggtgacgaag | aactgaccat gctggcattt | 420 |
| gctattgcga | cgctgtatca | cgaaggcgaa | gaatttggca | ccggtccgat cctgatgatt | 480 |
| tcatacgccg | atggttcgga | agcacgtgtt | atcacctgga | aaaagattga tctgccgtat | 540 |
| gtggacgttg | tcagcacgga | aaaggaaatg | atcaaacgct | tcctgcgtgt ggttcgtgaa | 600 |
| aaggatccgg | acgtgctgat | tacctataac | ggcgataatt | ttgacttcgc ctacctgaaa | 660 |
| aagcgttgcg | aagaactggg | tatcaaattt | acgctgggcc | gcgatggtag cgaaccgaaa | 720 |
| attcagcgca | tgggcgaccg | ttttgcagtc | gaagtgaaag | gtcgcatcca tttcgatctg | 780 |
| tacccggtta | tccgtcgcac | cattaacctg | ccgacctata | cgctggaagc tgtctacgaa | 840 |
| gcggtgttcg | gcaaaccgaa | ggaaaaagtg | tatgcagaag | aaattgccca ggcttgggaa | 900 |
| tcaggcgaag | gtctggaacg | cgtggcacgt | tattcgatgg | aagatgctaa agttacgtac | 960 |
| gaactgggtc | gcgaattttt | cccgatggaa | gcgcagctga | gccgtctgat tggccaaagc | 1020 |
| ctgtgggatg | tttctcgcag | ctctaccggt | aacctggtcg | aatggtttct gctgcgcaag | 1080 |
| gcgtataaac | gtaacgaact | ggccccgaat | aaaccggatg | aacgtgaact ggcacgtcgc | 1140 |
| cgtggcggtt | atgctggcgg | ttacgttaaa | gaaccggaac | gtggtctgtg ggataatatc | 1200 |
| gtgtatctgg | acttccgcag | ttcggccgtg | tccattatca | ttacccataa cgttagtccg | 1260 |
| gatacgctga | tcgcgaagg | ctgcaaagaa | tatgacgttg | cgccggaagt cggtcacaag | 1320 |
| ttttgtaaag | attttccggg | cttcattccg | tccctgctgg | gtgacctgct ggaagaacgc | 1380 |
| cagaagatca | gcgtaagat | gaaagccacc | gtggatccgc | tggaaaagaa actgctggac | 1440 |
| tatcgccaac | gtctgatcaa | aattctggcg | aacagctttt | atggctatta cggttacgcc | 1500 |
| aaggcacgct | ggtattgcaa | agaatgtgcc | gaatctgtga | ccgcatgggg ccgcgaatac | 1560 |
| attgaaatgg | tgatccgtga | actggaagaa | aagttcggtt | tcaaggttct gtatgcggat | 1620 |
| accgacggcc | tgcatgccac | gatcccgggt | gctgatgcgg | aaaccgtgaa aaagaaagcg | 1680 |
| aaggaatttc | tgaagtacat | caacccgaag | ctgccgggcc | tgctggaact ggaatatgaa | 1740 |
| ggcttttacg | tccgtggctt | tttcgtgacg | aagaaaaagt | atgcggttat cgatgaagaa | 1800 |
| ggcaaaatta | ccacgcgcgg | tctggaaatc | gtgcgccgtg | actggtcaga aattgctaaa | 1860 |
| gaaacccagg | cgcgtgtcct | ggaagccatc | ctgaaacacg | gtgatgtgga agaagcggtc | 1920 |
| cgcattgtga | agaagttac | ggaaaagctg | tcgaaatatg | aagtcccgcc ggaaaaactg | 1980 |
| gtgatccatg | aacaaattac | ccgcgatctg | cgtgactaca | aagcaacggg tccgcacgtt | 2040 |

-continued

```
gcagtcgcaa agcgtctggc agcacgtggt gtgaaaattc gtccgggcac cgttatcagt    2100
tatattgtcc tgaaaggctc cggtcgcatc ggtgatcgtg ccattccggc agatgaattt    2160
gacccgacga acaccgcta tgacgccgaa tattacatcg aaaatcaggt gctgccggca     2220
gttgaacgca ttctgaaggc ttttggctac cgtaaagaag atctgcgcta tcaaaaaacc    2280
aagcaagtcg gtctgggtgc gtggctgaaa gtcaagggca aaaataa                  2328
```

<210> SEQ ID NO 8
<211> LENGTH: 2325
<212> TYPE: DNA
<213> ORGANISM: Thermococcus kodakarensis kod1
<220> FEATURE:
<221> NAME/KEY: misc_feature
<223> OTHER INFORMATION: KODexo- DNA polymerase

<400> SEQUENCE: 8

```
atgatcctcg acactgacta cataaccgag gatggaaagc ctgtcataag aattttcaag     60
aaggaaaacg gcgagtttaa gattgagtac gaccggactt tgaacccta cttctacgcc     120 ctcctgaagg acgattctgc cattgaggaa gtcaagaaga taaccgccga gaggcacggg    180
acggttgtaa cggttaagcg ggttgaaaag gttcagaaga agttcctcgg agaccagtt    240 gaggtctgga aactctactt tactcatccg caggacgtcc cagcgataag ggacaagata    300
cgagagcatc cagcagttat tgacatctac gagtacgaca tacccttcgc caagcgctac    360
ctcatagaca agggattagt gccaatggaa ggcgacgagg agctgaaaat gctcgccttc    420
gctattgcga ctctctacca tgagggcgag gagttcgccg aggggccaat ccttatgata    480
agctacgccg acgaggaagg ggccagggtg ataacttgga agaacgtgga tctcccctac    540
gttgacgtcg tctcgacgga gagggagatg ataaagcgct tcctccgtgt tgtgaaggag    600
aaagacccgg acgttctcat aacctacaac ggcgacaact tcgacttcgc ctatctgaaa    660
aagcgctgtg aaaagctcgg aataaacttc gccctcggaa gggatggaag cgagccgaag    720
attcagagga tgggcgacag gtttgccgtc gaagtgaagg acggataca cttcgatctc    780 tatcctgtga taagacggac gataaacctg cccacataca cgcttgaggc cgtttatgaa    840
gccgtcttcg gtcagccgaa ggagaaggtt tacgctgagg aaataaccac agcctgggaa    900
accggcgaga accttgagag agtcgcccgc tactcgatgg aagatgcgaa ggtcacatac    960
gagcttggga aggagttcct tccgatggag gcccagcttt ctcgcttaat cggccagtcc    1020
ctctgggacg tctcccgctc cagcactggc aacctcgttg agtggttcct cctcaggaag    1080
gcctatgaga ggaatgagct ggccccgaac aagcccgatg aaaaggagct ggccagaaga    1140
cggcagagct atgaaggagg ctatgtaaaa gagcccgaga gagggttgtg ggagaacata    1200
gtgtacctag attttagatc cctgtacccc tcaatcatca tcacccacaa cgtctcgccg    1260
gatacgctca cagagaagg atgcaaggaa tatgacgttg ccccacaggt cggccaccgc    1320
ttctgcaagg acttcccagg atttatcccg agcctgcttg agacctcct agaggagagg    1380 cagaagataa agaagaagat gaaggccacg attgacccga tcgagaggaa gctcctcgat    1440
tacaggcaga gggccatcaa gatcctggca aacagctact acggttacta cggctatgca    1500
agggcgcgct ggtactgcaa ggagtgtgca gagagcgtaa cggcctgggg aagggagtac    1560
ataacgatga ccatcaagga gatagaggaa aagtacggct ttaaggtaat ctacagcgac    1620
accgacggat ttttgccac aatacctgga gccgatgctg aaaccgtcaa aaagaaggct    1680
atggagttcc tcaagtatat caacgccaaa cttccgggcg cgcttgagct cgagtacgag    1740
```

```
ggcttctaca aacgcggctt cttcgtcacg aagaagaagt atgcggtgat agacgaggaa    1800
ggcaagataa caacgcgcgg acttgagatt gtgaggcgtg actggagcga gatagcgaaa    1860
gagacgcagg cgagggttct tgaagctttg ctaaaggacg gtgacgtcga aaggccgtg     1920 aggatagtca aagaagttac cgaaaagctg agcaagtacg aggttccgcc ggagaagctg    1980
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaagggaa cttga                    2325

<210> SEQ ID NO 9
<211> LENGTH: 50
<212> TYPE: DNA
<213> ORGANISM: Artificial Sequence
<220> FEATURE:
<223> OTHER INFORMATION: Primer_FAM_50nt oligonucleotide primer

<400> SEQUENCE: 9
agtgaattcg agctcggtac ccggggatcc tctagagtcg acctgcaggc               50

<210> SEQ ID NO 10
<211> LENGTH: 50
<212> TYPE: DNA
<213> ORGANISM: Artificial Sequence
<220> FEATURE:
<223> OTHER INFORMATION: M13-Fam-50 oligonucleotide primer

<400> SEQUENCE: 10
cgagcacgta taacgtgctt tcctcgttgg aatcagagcg ggagctaaac               50

<210> SEQ ID NO 11
<211> LENGTH: 67
<212> TYPE: DNA
<213> ORGANISM: Artificial Sequence
<220> FEATURE:
<223> OTHER INFORMATION: Temp_(A)67nt oligonucleotide template

<400> SEQUENCE: 11
ttgctcgttt gctgggagcc tgcaggtcga ctctagagga tccccgggta ccgagctcga    60
attcact                                                              67

<210> SEQ ID NO 12
<211> LENGTH: 67
<212> TYPE: DNA
<213> ORGANISM: Artificial Sequence
<220> FEATURE:
<223> OTHER INFORMATION: Temp(G)_67nt oligonucleotide template

<400> SEQUENCE: 12
ttgctcgttt gctaaaggcc tgcaggtcga ctctagagga tccccgggta ccgagctcga    60
attcact                                                              67

<210> SEQ ID NO 13
<211> LENGTH: 67
<212> TYPE: DNA
<213> ORGANISM: Artificial Sequence
<220> FEATURE:
<223> OTHER INFORMATION: Temp(T)_67nt oligonucleotide template
```

```
<400> SEQUENCE: 13
ttgctcgttt gctgggtgcc tgcaggtcga ctctagagga tccccgggta ccgagctcga        60
attcact                                                                  67

<210> SEQ ID NO 14
<211> LENGTH: 67
<212> TYPE: DNA
<213> ORGANISM: Artificial Sequence
<220> FEATURE:
<223> OTHER INFORMATION: Temp(C)_67nt oligonucleotide template

<400> SEQUENCE: 14
ttgctcgttt gctgggcgcc tgcaggtcga ctctagagga tccccgggta ccgagctcga        60
attcact                                                                  67

<210> SEQ ID NO 15
<211> LENGTH: 149
<212> TYPE: DNA
<213> ORGANISM: Artificial Sequence
<220> FEATURE:
<223> OTHER INFORMATION: M13-100nt oligonucleotide template

<400> SEQUENCE: 15
atggacagac tcttttactc ggtggcctca ctgattataa aaacacttct caagattctg        60
gcgtaccgtt cctgtctaaa atccctttaa tcggcctcct gtttagtccc gctctgattc       120
caacgaggaa agcacgttat acgtgctcg                                         149
```